US006506756B2

(12) United States Patent
Shih et al.

(10) Patent No.: US 6,506,756 B2
(45) Date of Patent: Jan. 14, 2003

(54) SUBSTITUTED IMIDAZOLES AS DUAL HISTAMINE $H_1$ AND $H_3$ AGONISTS OR ANTAGONISTS

(75) Inventors: Neng-Yang Shih, North Caldwell, NJ (US); Daniel M. Solomon, Edison, NJ (US); John J. Piwinski, Clinton Township, NJ (US); Andrew T. Lupo, Jr., Emerson, NJ (US); Michael J. Green, Half Moon Bay, CA (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/954,867

(22) Filed: Sep. 18, 2001

(65) Prior Publication Data

US 2002/0086859 A1 Jul. 4, 2002

Related U.S. Application Data

(60) Provisional application No. 60/234,053, filed on Sep. 20, 2000.

(51) Int. Cl.$^7$ .................. C07D 401/12; C07D 401/14; A61K 31/445; A61P 25/00
(52) U.S. Cl. .................. 514/253.03; 546/93; 544/361; 514/290
(58) Field of Search ................. 546/93; 514/253.03, 514/290; 544/361

(56) References Cited

U.S. PATENT DOCUMENTS

| | | | |
|---|---|---|---|
| 4,767,778 A | 8/1988 | Arrang et al. | 514/397 |
| 5,352,707 A | 10/1994 | Pompni et al. | 514/651 |
| 5,869,479 A | 2/1999 | Kreutner et al. | 514/212 |

FOREIGN PATENT DOCUMENTS

| | | |
|---|---|---|
| EP | 0 341 860 A1 | 4/1989 |
| EP | 0448 765 B1 | 3/1990 |
| EP | 0 420 396 B1 | 7/1990 |
| WO | WO 93/01812 | 2/1993 |
| WO | WO 93/12093 | 6/1993 |
| WO | WO 95/14007 | 5/1995 |
| WO | WO 96/29315 | 9/1996 |
| WO | WO 98/58646 | 12/1998 |
| WO | WO 00/05215 | 2/2000 |

OTHER PUBLICATIONS

Leurs et al. Therapeutic potential of histamine H3 receptor agonists and antagonists, Trends Pharm. Sci. 19: 177–83 (1998).*
Sasse, A., Bioorganic & Medicinal Chemistry, vol. 8, (Partial) Agonist/Antagonist Properties of Novel Diarylalkyl Carbamates on Histamine H3 Receptors, pp 1139–1149 (2000).
Stark, H., Drugs of the Future, vol. 21(5) Developments of Histamine H3–receptor antagonists, pp 507–520 (1996).
Howson, Bioorganic & Medicinal Chemistry Letters, Two Novel, Potent and Selective Histamine H3 Receptor Agonists, vol. 2, pp. 77–78, 1992.
Stark, J. Med. Chem. , Novel Carbamates as Potent Histamine H3 Receptor Antagonists with High in Vitro and Oral In Vivo Activity, 39, pp. 1157–1163.
Sasse, Bioorganic & Medicinal Chemistry, (Partial) Agonist/Antagonist Properties of Novel Diarylalkyl, vol. 8 (2000) pp. 1139–1149.
Bagley, J. Med. Chem. 1991, New 1–(Heterocyclylalkyl)–4–(Propionanilido)–4–Piperidinyl, 34, pp 827–941.
Huls, Bioorganic & Medicinal Chemistry Letters, Diphenylmethyl Ethers: Synthesis and Histamine, vol. 6, No. 16, pp. 2013–2018, 1996.
Buschauer, J. Med. Chem. 1989, Synthesis and in Vitro Pharmacology of Arpromidine, 32, pp 1963–1970, 1989.
Schulze, Arch. Pharm. (Weinheim), Synthese und kombinierte H1/H2–antagonistische, vol. 327, pp. 455–462, 1994.
Schulze, European Journal of Pharmaceutical Sciences, Combined histamine H1/H2 receptor antagonists, vol. 6, pp. 177–186, 1998.
van der Goot, Eur J. Med. Chem. , Isothiourea analogues of histamine as potent agonists, vol. 27, pp. 511–517, 1992.
Walczynski, II Farmaco, Non–imidazole histamine H3 ligands, Vo. 54, pp. 684–694, 1999.
Brown, Br. J. Pharmac. , Pharmacological studies with SK & F 93944, vo., 87, pp. 569–578, 1986.
West, Molecular Pharmacology, Identificatin of Two H3–Histamine Receptor Subtypes, vol. 38, pp. 610–613, 1990.
Clapham, Brit. J. Pharm. Suppl. , Ability of the Selective Histamine H3 Receptor Antagonist, vol. 110, pp. Abs. 65P, 00/00, 1993.
Yokoyama, European Journal of Pharmacology, Effect of Thioperamide, vol. 234, pp 129–133, 1993.
Schlicker, Br. J. Pharmacol., Novel Histamine H3 Receptor Antagonists, vol. 112, pp. 1043–1048, 1994.
Leurs, Progre. Drug. Res. , The Histamine H3–Receptor, vol. 39, pp. 127–165, 00/00, 1992.
Lipp, Histamine Receptor, Pharmacochemistry of H3–Receptors, pp. 57–72, 00/00, 1992.
Stark, European Journal of Pharmaceutical Sciences, New potent Histamine H3–Receptor vol. 3, pp. 95–104, 1995.

* cited by examiner

Primary Examiner—Mukund J. Shah
Assistant Examiner—Hong Liu
(74) Attorney, Agent, or Firm—Palaiyur S. Kalyanaraman

(57) ABSTRACT

The present invention discloses novel substituted imidazole compounds which have dual histamine-$H_1$ and $H_3$ receptor antagonist activity as well as methods for preparing such compounds. In another embodiment, the invention discloses pharmaceutical compositions comprising such imidazoles as well as methods of using them to treat allergy, inflammatory and CNS-related diseases and others.

21 Claims, No Drawings

SUBSTITUTED IMIDAZOLES AS DUAL HISTAMINE $H_1$ AND $H_3$ AGONISTS OR ANTAGONISTS

This application claims the benefit of U.S. Provisional Application No. 60/234,053, filed on Sep. 20, 2000.

FIELD OF THE INVENTION

The present invention relates to novel substituted imidazole compounds having valuable pharmacological properties, especially against inflammatory diseases and allergic conditions. Compounds of this invention are antagonists of the histamine receptors. Some are antagonists of the histamine-$H_1$ receptors. Some are antagonists of the histamine-$H_3$ receptors. Some are antagonists of both the $H_1$ and $H_3$ receptors, in other words dual $H_1$ and $H_3$ receptor antagonists. The invention disclosed in this application claims priority from provisional application, Ser. No. 60/230,053 filed Sep. 20, 2000, and is related to that in pending provisional applications, Ser. No. 60/234,039, Ser. No. 60/234,040, and Ser. No. 60/234,038, all filed on Sep. 20, 2000.

BACKGROUND OF THE INVENTION

The histamine receptors, $H_1$, $H_2$ and $H_3$ are well-identified forms. The $H_1$ receptors are those that mediate the response antagonized by conventional antihistamines. $H_1$ receptors are present, for example, in the ileum, the skin, and the bronchial smooth muscle of humans and other mammals. A well-known antagonist of $H_1$ receptors is loratadine, commercially available under the tradename CLARITIN® from Schering-Plough Corporation, Madison, N.J. Through $H_2$ receptor-mediated responses, histamine stimulates gastric acid secretion in mammals and the chronotropic effect in isolated mammalian atria.

$H_3$ receptor sites are found on sympathetic nerves, where they modulate sympathetic neurotransmission and attenuate a variety of end organ responses under control of the sympathetic nervous system. Specifically, $H_3$ receptor activation by histamine attenuates nonepinephrine outflow to resistance and capacitance vessels, causing vasodilatation.

U.S. Pat. No. 4,767,778 (Arrang et al.) discloses certain imidazoles that behave as agonists of the $H_3$ receptors in rat brain. European Patent Application No. 0 420 396 A2 (Smith Kline & French Laboratories Limited) and Howson et al. (*Bioorg. & Med. Chem. Letters*, (1992), Vol. 2 No. 1, pp. 77–78) describe imidazole derivatives having an amidine group as $H_3$ agonists. Van der Groot et al. (*Eur. J. Med. Chem.* (1992) Vol. 27, pp. 511–517) describe isothiourea analogs of histamine as potent agonists or antagonists of the histamine-$H_3$ receptor, and these isothiourea analogs of histamine overlap in part with those of the two references cited above. Clapham et al. ["Ability of Histamine-$H_3$ Receptor Antagonists to Improve Cognition and to Increase Acetylcholine Release in vivo in the Rat", *British Assn. for Psychopharmacology*, Jul. 25–28 (1993), reported in *J. Psychopharmacol.* (Abstr. Book), A17] describe the ability of histamine-$H_3$ receptor antagonists to improve cognition and to increase release of acetylcholine in vivo in the rat. Clapham et al. ["Ability of the selective Histamine-$H_3$ Receptor Antagonist Thioperamide to improve Short-term Memory and Reversal Learning in the Rat", *Brit. J. Pharm. Suppl.*, 1993, 110, Abstract 65P] present results showing that thioperamide can improve short-term memory and reversal learning in the rat and implicate the involvement of $H_3$ receptors in the modulation of cognitive function. Yokoyama et al. ["Effect of Thioperamide, a Histamine-$H_3$ Receptor Antagonist, on Electrically Induced Convulsions in Mice", *Eur. J. Pharmacol.*, (1993), Vol. 234, pp. 129–133] report how thioperamide decreased the duration of each phase of convulsion and raised the electroconvulsive threshold, and go on to suggest that these and other findings support the hypothesis that the central histaminergic system is involved in the inhibition of seizures. International Patent Publication No. WO 9301812-A1 (SmithKline Beecham PLC) describes the use of S-[3-(4(5)-imidazolyl)propyl] isothiourea as a histamine-$H_3$ antagonist, especially for treating cognitive disorders, e.g. Alzheimer's disease and age-related memory impairment. Schlicker et al. ["Novel Histamine-$H_3$ Receptor Antagonists: Affinities in an $H_3$ Receptor Binding Assay and Potencies in Two Functional $H_3$ Receptor Models", *British J. Pharmacol.*, (1994), Vol. 112, 1043–1048] describe a number of imidazolylalkyl compounds wherein the imidazolylalkyl group is bonded to a guanidine group, an ester group, an amide group, a thioamide group and a urea group, and compared these to thioperamide. Leurs et al. ["The Histamine-$H_3$-receptor: A Target for Developing New Drugs", Progr. Drug Res. (1992), Vol. 39, pp.127–165] and Lipp et al. ["Pharmacochemistry of $H_3$-receptors" in *The Histamine Receptor*, eds.: Schwartz and Haas, Wiley-Liss, N.Y. (1992), pp. 57–72] review a variety of synthetic $H_3$ receptor antagonists, and Lipp et al. (ibid.) have proposed the necessary structural requirements for an $H_3$ receptor antagonist.

WO 95/14007 claims $H_3$ receptor antagonists of the formula

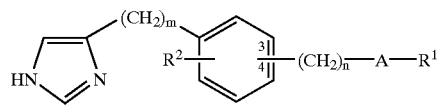

wherein A, m, n, $R^1$ and $R^2$ are defined therein. The compounds are disclosed as being useful for treating various disorders, in particular such caused by allergy-induced responses.

WO 93/12093 discloses imidazolylmethyl piperazines and diazepines as $H_3$ antagonists. U.S. patent application, Ser. No. 08/965,754, filed Nov. 7, 1997, discloses imidazolylalkyl substituted heterocyclic ring compounds as $H_3$ receptor antagonists. U.S. patent application, Ser. No. 08/966,344, filed Nov. 7, 1997, discloses phenylalkylimidazoles as $H_3$ receptor antagonists.

WO 96/29315 (PCT/FR96/00432) discloses certain N-imidazolylalkyl compounds containing phenyl moieties attached.

Also disclosing $H_3$ receptor antagonists are: H. Stark et al, *Eur. J. of Pharmaceutical Sciences* (1995) 3, 95–104; H. Stark et al, *J. Med. Chem.*, (1996) 39, 1157–1163; H. Stark et al, *Arch. Pharm. Pharm. Med. Chem.*, (1998) 331, 211–218; and A. Sasse et al, *Bioorganic & Medicinal Chem.*, (2000) 8, 1139–1149.

Reference is also made to J. R. Bagley et al. *Journal of Medicinal Chemistry*, (1991), Vol. 34, 827–841, which discloses, among others, N-(imidazolylalkyl) substituted cyclic amine compounds useful as analgesics such as the amine compound with the formula:

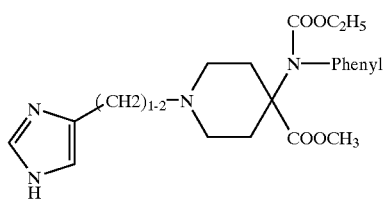

Pending U.S. patent application, Ser. No. 09/173,642, filed Oct. 16, 1998 (R. Wolin et al.), discloses N-(imidazolylalkyl) substituted cyclic amine compounds having $H_3$ antagonist activity.

A. Huls et al., *Bioorg. & Med. Chem. Letters*, 6 (1996), 2013–2018 disclose imidazole compounds containing diphenyl ether moieties as $H_3$ receptor antagonists. The compounds are additionally disclosed to have $H_1$ receptor antagonist activity. An example compound from that publication is:

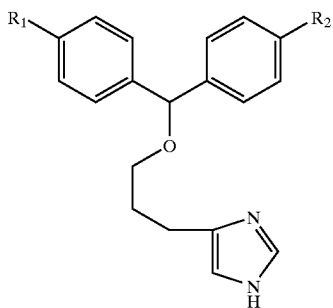

where $R_1$ and $R_2$ are defined therein.

A. Buschauer, *J. Med. Chem.*, 32 (1989),1963–1970 disclose, among others, $H_2$ receptor antagonists of the type:

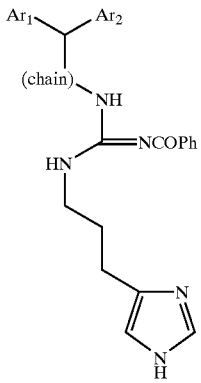

where $Ar_1$ and $Ar_2$ may be phenyl and/or pyridyl. EPO 448,765 A1 (published Mar. 30, 1990) discloses neuropeptide-Y antagonist imidazoles of the type:

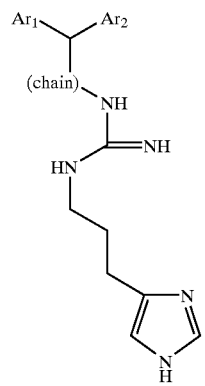

where $Ar_1$ and $Ar_2$ may be phenyl and/or pyridyl.

WO 98-58646 (assigned to Novo Nordisk A/S) discloses somatostatin SSTR4 receptor antagonist compounds of the type:

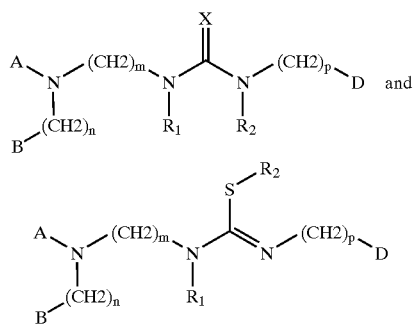

wherein m is 2–6; n is 1–3; p is 1–6; $R_1$ and $R_2$ are independently H or C1–C6 alkyl optionally substituted with halogen, amino, hydroxy, alkoxy or aryl; X is S, O, NH, NCOPh or N(CN); A is aryl optionally substituted with halogen, amino, hydroxy, nitro, C1–6 alkyl, C1–6 alkoxy, or aryl; and B and D are independently aryl optionally substituted with halogen, amino, hydroxy, C1–6 alkyl, C1–6 alkoxy, or aryl.

Compounds have been reported in the literature as having activity against both $H_1$ and $H_2$ receptors, i.e. dual antagonists against $H_1$ and $H_2$ receptors. Thus, for example, F. Schulze et al., *European J. of Pharmaceutical Sciences*, 6 (1998), 177–186 report combined $H_1/H_2$ receptor antagonists. Other references in this category include F. Schulze et al., *Arch. Pharm.* (Weinheim), 327 (1994), 455–462; C. Wolf et al., *Arch. Pharm. Pharm. Med. Chem.*, 329 (1996), 87–94; and C. Wolf et al., *European J. of Pharmaceutical Sciences*, 6 (1998), 177–186. Non-imidazole histamine $H_3$ ligands, particularly substituted benzothiazole derivatives as $H_3$ antagonists and $H_1$ blocking activities have been reported by K. Walczynski et al, II Farmaco, 54 (1999), 684–694.

It would be useful to have compounds which are therapeutically effective as antagonists of both the $H_1$ and $H_3$ histamine receptors. The only such reported activity has been through a combination of two different chemical entities, one showing activity against $H_1$ receptors and the other showing activity against $H_3$ receptors. Thus, for example, U.S. Pat. No. 5,869,479 (issued Feb. 9, 1999 to Schering Corporation) discloses the combination of a histamine-$H_1$ receptor antagonist and a histamine-$H_3$ receptor antagonist for the treatment of allergy-induced airway responses.

Pending provisional patent application, Ser. No.60/234,039, filed Sep. 20, 2000, discloses novel imidazole compounds having $H_3$ as well as dual $H_1$ and $H_3$ antagonist activity. The compounds disclosed therein have general formula in which an imidazole is linked to two cyclic moieties via intermediary moiety or moieties at least one of which intermediary moiety or moieties is a cyclic moiety.

Pending provisional patent application, Ser. No. 60/234,038, filed Sep. 20, 2000, discloses novel imidazole compounds having $H_3$ as well as dual $H_1$ and $H_3$ antagonist activity. The compounds disclosed therein have general formula in which an imidazole is linked to a tricyclic moiety via intermediary moiety or moieties which intermediary moiety or moieties are all acyclic moieties.

Pending provisional patent application, Ser. No. 60/234,040, filed Sep. 20, 2000, discloses novel imidazole compounds having $H_3$ as well as dual $H_1$ and $H_3$ antagonist activity. The compounds disclosed therein have general formula in which an imidazole is linked to two cyclic moieties via intermediary moiety or moieties which intermediary moiety or moieties are acyclic.

It would be a welcome contribution to the art to have novel substituted imidazole compounds.

It would be useful to have the same chemical entity showing dual activity against both $H_1$ and $H_3$ receptors.

It would be useful to have novel substituted imidazoles showing activity against both $H_1$ and $H_3$ receptors.

U.S. Pat. No. 5,801,175 (issued Sep. 1, 1998; Assignee: Schering Corporation) discloses compounds having the following general structural formula as inhibitors of G-protein function and for the treatment of proliferative diseases:

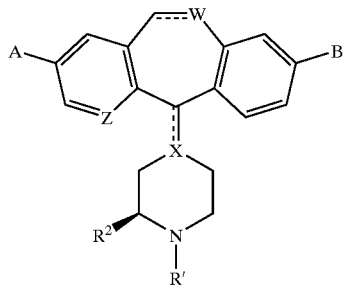

where A, B, W, X, Z, $R^1$ and $R^2$ are defined therein. Imidazoles as well as other types of compounds are disclosed therein.

U.S. Pat. No. 5,719,148 (issued Feb. 17, 1998; Assignee: Schering Corporation), U.S. Pat. No. 4,826,853 (issued May 2, 1989; Assignee: Schering Corporation), and WO 96/30363 (published Oct. 3, 1996; Assignee: Schering Corporation) disclose compounds having the following general structural formula as inhibitors of G-protein function and for the treatment of proliferative diseases:

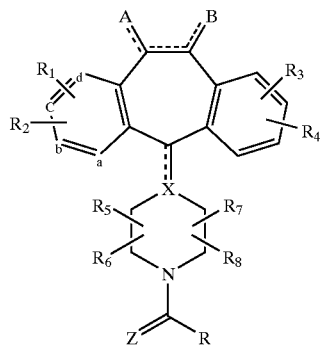

where the various elements are defined therein. Imidazoles as well as other types of compounds are disclosed therein. The above-noted U.S. Pat. Nos. 5,801,175 and 4,826,853 and WO 96/30363 are incorporated herein by reference.

It has now been found that certain imidazole compounds disclosed or referred-to in the above-noted U.S. Pat. Nos. 5,801,175 and 4,826,853 and WO 96/30363 surprisingly exhibit $H_3$ as well as dual $H_1$ and $H_3$ antagonist activity. The present application discloses surprising potency and use of such imidazoles which have the general formula in which an imidazole is linked to a tricyclic moiety via intermediary moiety or moieties at least one of which intermediary moiety or moieties is a cyclic moiety. The $H_3$ activity as well as dual $H_1/H_3$ activity of such compounds have not been disclosed before.

SUMMARY OF THE INVENTION

In one embodiment, this invention provides substituted imidazole compounds having $H_3$ antagonist activity as well as dual $H_1$ and $H_3$ antagonist activity. The inventive compounds are substituted imidazoles wherein the imidazole is linked to a tricyclic moiety via intermediary moiety or moieties at least one of said intermediary moiety or moieties is a cyclic moiety. The compounds have the general structure shown in Formula I:

Formula I

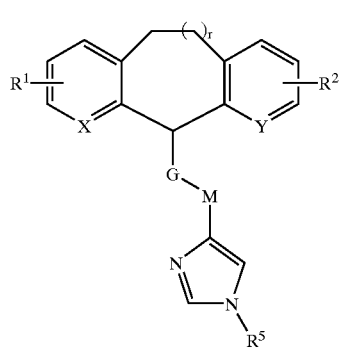

wherein:

f=0, 1 or 2;

X and Y are independently selected from the group consisting of N, CH or N-oxide;

G is a moiety selected from the group consisting of the moieties II, III and IV with the top end of said II, III and IV being linked to the tricyclic moiety and the bottom end of II, III and IV being linked to M:

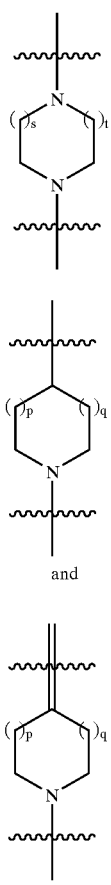

where s=t=1 or 2; and p=q=0, 1 or 2;

M is a moiety selected from the group consisting of $C_1$–$C_8$ alkyl; —C(O)—$(CH_2)_y$—; —$(CH_2)_x$—A—$(CH_2)_y$—; —C(O)—O—$(CH_2)_d$—; and —C(O)—$NR^3$—$(CH_2)_d$—; where A=O, $S(O)_r$—, and —$NR^4$—;

n=0, 1, 2 or 3;

x is a whole number in the range 2–5;

y is a whole number in the range 0–5;

d is a number in the range 0–5;

r=0, 1 or 2;

$R^1$ and $R^2$ may each number 1–3 and are independently selected from the group consisting of hydrogen, lower alkyl, lower alkoxy, halogen, $OCF_3$, $OCHF_2$, —OH, and —$N(R^4)_2$;

$R^3$ is selected from the group consisting of hydrogen, lower alkyl, and polyhaloloweralkyl;

$R^4$ is selected from hydrogen, lower alkyl, polyhalolower alkyl; and $R^5$ is H, $C_1$–$C_6$ alkyl or OH.

When used herein, the following terms have the given meanings:

lower alkyl (including the alkyl portions of lower alkoxy)—represents a straight or branched, saturated hydrocarbon chain having from 1 to 6 carbon atoms, preferably from 1 to 4;

aryl—represents a carbocyclic group having from 6 to 14 carbon atoms and having at least one benzenoid ring, with all available substitutable aromatic carbon atoms of the carbocyclic group being intended as possible points of attachment. Preferred aryl groups include 1-naphthyl, 2-naphthyl and indanyl, and especially phenyl and substituted phenyl;

cycloalkyl—represents a saturated carbocyclic ring having from 3 to 8 carbon atoms, preferably 5 or 6, optionally substituted.

heterocyclic—represents, in addition to the heteroaryl groups defined below, saturated and unsaturated cyclic organic groups having at least one O, S and/or N atom interrupting a carbocyclic ring structure that consists of one ring or two fused rings, wherein each ring is 5-, 6- or 7-membered and may or may not have double bonds that lack delocalized pi electrons, which ring structure has from 2 to 8, preferably from 3 to 6 carbon atoms, e.g., 2-3- or 4-piperidinyl, 2- or 3-piperazinyl, 2- or 3-morpholinyl, or 2- or 3-thiomorpholinyl;

halogen—represents fluorine, chlorine, bromine and iodine;

heteroaryl—represents a cyclic organic group having at least one O, S and/or N atom interrupting a carbocyclic ring structure and having a sufficient number of delocalized pi electrons to provide aromatic character, with the aromatic heterocyclic group having from 2 to 14, preferably 4 or 5 carbon atoms, e.g., 2-, 3- or 4-pyridyl, 2- or 3-furyl, 2- or 3-thienyl, 2-, 4- or 5-thiazolyl, 2- or 4-imidazolyl, 2-, 4- or 5-pyrimidinyl, 2-pyrazinyl, or 3- or 4-pyridazinyl, etc. Preferred heteroaryl groups are 2-, 3- and 4-pyridyl; such heteroaryl groups may also be optionally substituted.

The term "substituted", unless otherwise defined, refers to chemically suitable substitution with moieties such as, for example, alkyl, alkoxy, —$CF_3$, halogen or aryl. Furthermore, the term "alkyl", when chemically suitable, also includes alkylene and related moieties.

Also included in the invention are tautomers, enantiomers and other optical isomers of compounds of Formula I, as well as pharmaceutically acceptable salts and solvates thereof.

A further feature of the invention is pharmaceutical compositions containing as active ingredient a compound of Formula I (or its salt, solvate or isomers) together with a pharmaceutically acceptable carrier or excipient.

The invention also provides methods for preparing compounds of Formula I, as well as methods for treating diseases such as, for example, inflammation, allergy, diseases of the GI-tract, cardiovascular disease, or disturbances of the central nervous system as well as allergy-induced airway (e.g., upper airway) responses, nasal congestion and obesity. The methods for treating comprise administering to a mammalian patient (including human and animals) suffering from said disease or diseases a therapeutically effective amount of a compound of Formula I, or pharmaceutical compositions comprising a compound of Formula I.

DETAILED DESCRIPTION OF THE INVENTION

In one embodiment, the present invention provides novel imidazole compounds of Formula I as compounds exhibiting $H_1$ antagonist activity, or $H_3$ antagonist activity or dual $H_1$ and $H_3$ antagonist activity:

Formula I
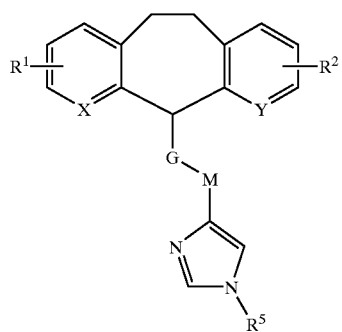
where the various symbols are as defined above. Representative compounds of the invention which exhibit $H_3$ antagonist activity are listed below:
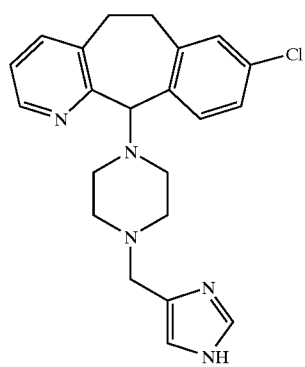
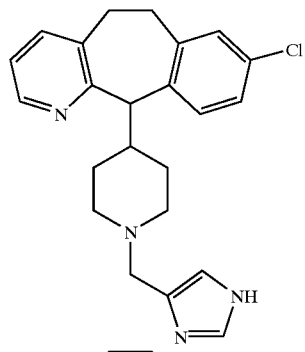
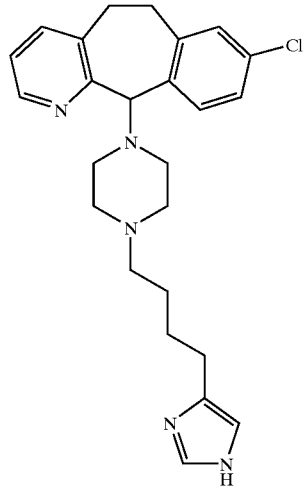
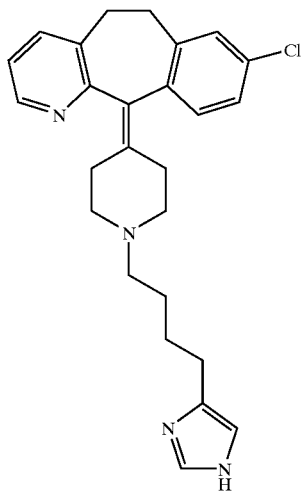
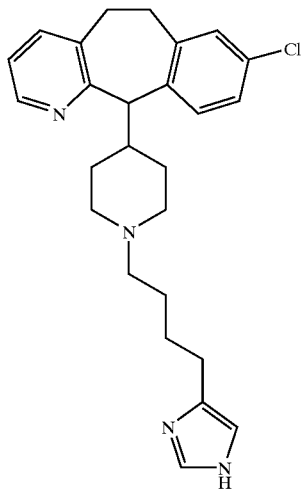
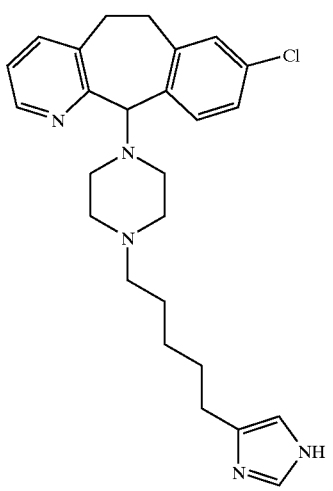

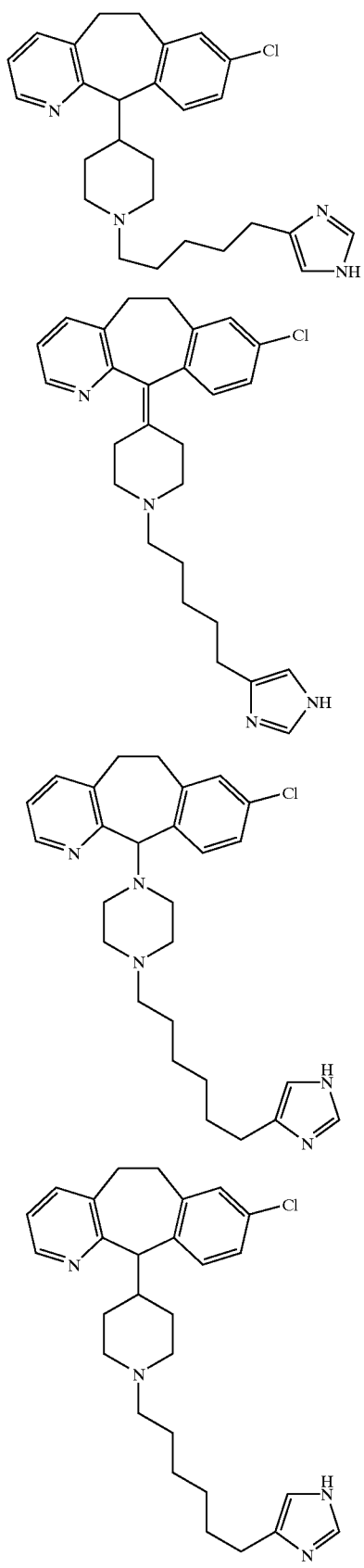
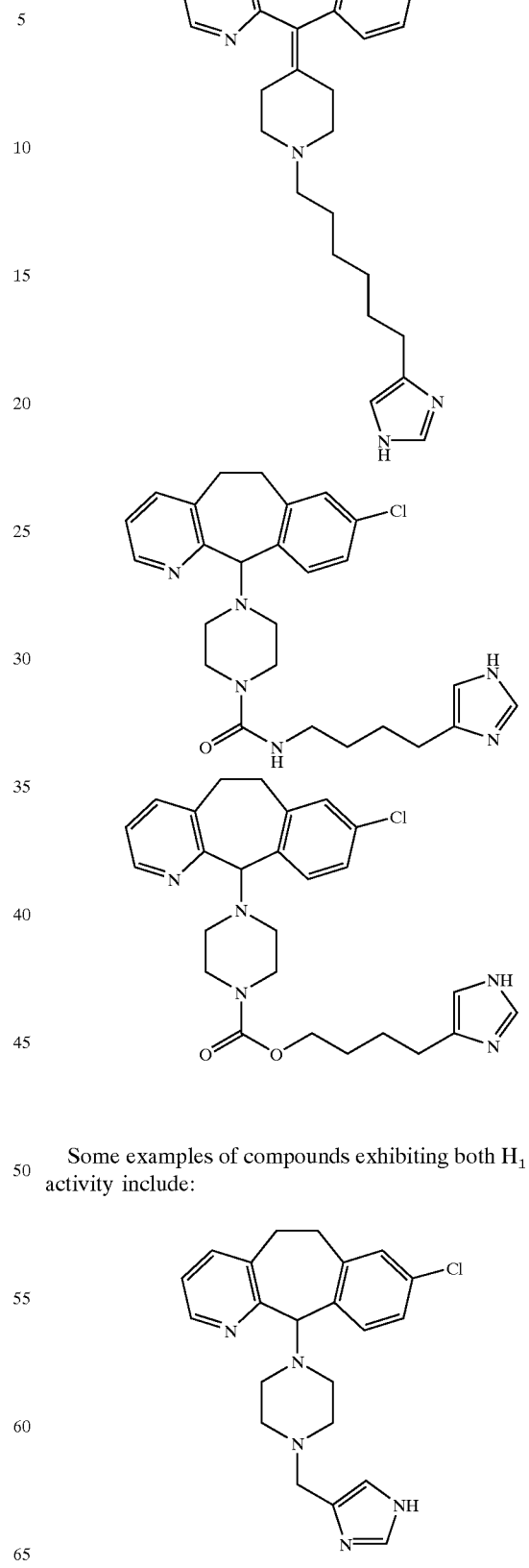
Some examples of compounds exhibiting both $H_1$ and $H_3$ activity include:
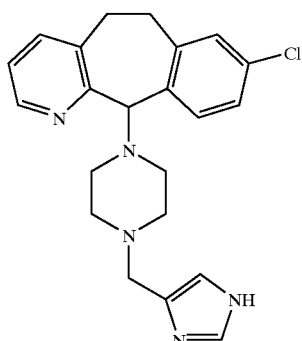

-continued
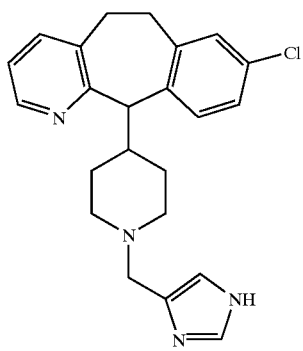
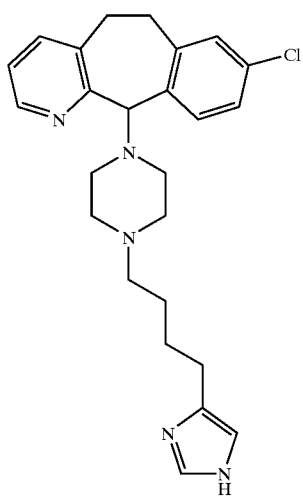
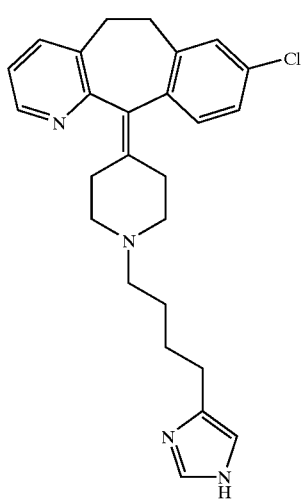
-continued
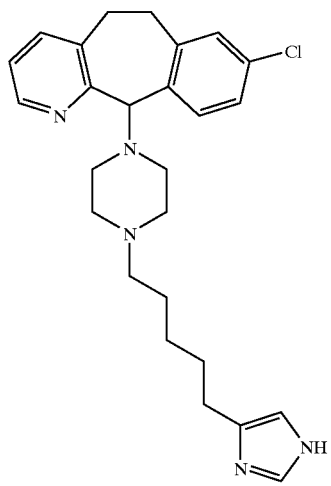
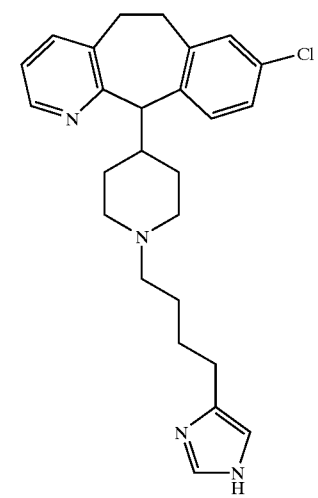
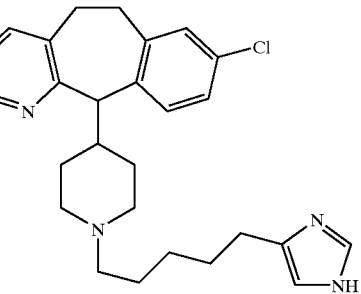

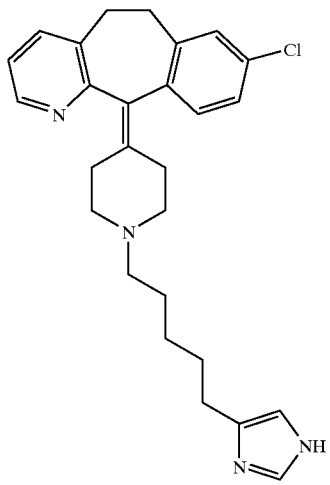
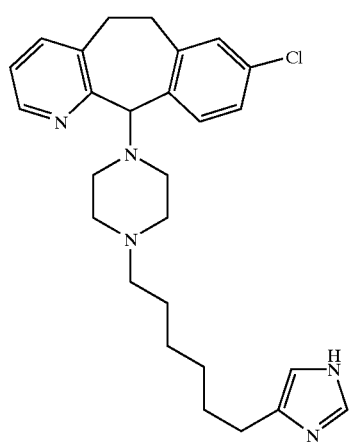
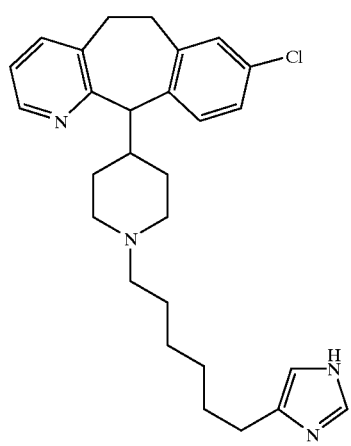
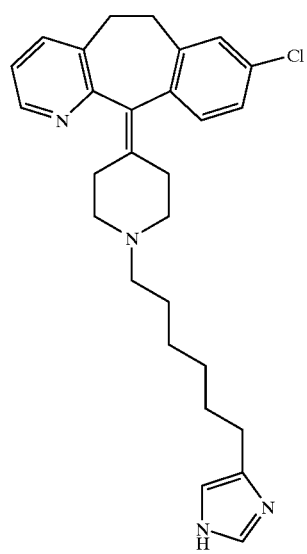
Representative compounds exhibiting $H_1$ antagonist activity include:
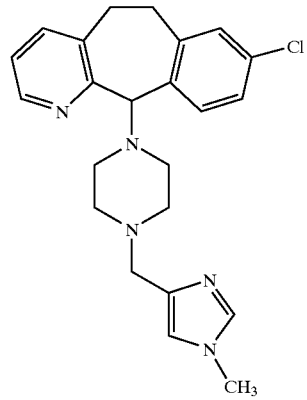

-continued

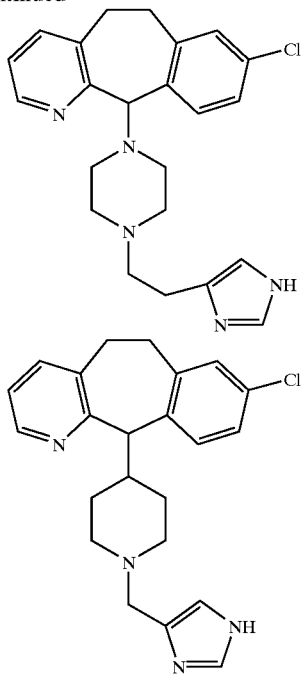

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

Depending upon the substituents on the inventive compounds, one may be able to form salts with bases too. Thus, for example, if there are carboxylic acid substituents in the molecule, salts may be formed with inorganic as well as organic bases such as, for example, NaOH, KOH, $NH_4OH$, tetraalkylammonium hydroxide, and the like.

As stated earlier, the invention includes tautomers, enantiomers and other stereoisomers of the compounds also. Thus, as one skilled in the art knows, certain imidazole compounds may exist in tautomeric forms. Such variations are contemplated to be within the scope of the invention.

Another embodiment of the invention discloses a method of making the substituted imidazoles disclosed above. The compounds may be prepared by several processes well known in the art. In one method, the imidazole part (designated "the left side component" herein for simplicity purposes) and the diaryl part (designated "the right side component" herein for simplicity purposes) may be prepared separately. The left side component and the right side component may contain reactive moieties attached to them which moieties are suitable to be reacted with each other under appropriate reaction conditions. Thus, for example, the left side component may contain a carbethoxy end, and the right side component may have an amine end. Under appropriate reaction conditions, the two components may be reacted together whereby an imidazole containing a diaryl alkyl moiety linked through an extended amide chain is obtained. Other substituted imidazoles may be similarly prepared.

Isolation of the compound at various stages of the reaction may be achieved by standard techniques such as, for example, filtration, evaporation of solvent and the like. Purification of the product, intermediate and the like, may also be performed by standard techniques such as recrystallization, distillation, sublimation, chromatography, conversion to a suitable derivative which may be recrystallized and converted back to the starting compound, and the like. Such techniques are well known to those skilled in the art.

The thus prepared compounds may be analyzed for their composition and purity as well as characterized by standard analytical techniques such as, for example, elemental analysis, NMR, mass spectroscopy, and IR spectra.

The inventive compounds can readily be evaluated to determine activity at both $H_1$ and $H_3$ receptors by known methods, such as, for example, E. A. Brown et al, *British J. Pharm.*, (1986) Vol. 80, 569. $H_3$ activity may be determined by, for example, the guinea pig brain membrane assay and the guinea pig neuronal ileum contraction assay, both of which are described in U.S. Pat. No. 5,352,707. Another useful assay for $H_3$ activity utilizes rat brain membranes and is described by West et al., ("Identification of Two $H_3$-Histamine Receptor Subtypes", *Molecular Pharmacology*, (1990), Vol. 33, 610–613. Several of the present compounds were found to have high $H_1$ and $H_3$ antagonist activity which is discussed more in the EXAMPLES section below.

In another embodiment, this invention provides pharmaceutical compositions comprising the above-described inventive imidazoles as an active ingredient. The pharmaceutical compositions generally additionally comprise a pharmaceutically acceptable carrier diluent, excipient or carrier (collectively referred to herein as carrier materials). Because of their $H_1$ and $H_3$ antagonist activity, such pharmaceutical compositions possess utility in treating allergy, inflammation, nasal congestion, hypertension, glaucoma, sleeping disorders, states of hyper- and hypo-motility of the gastrointestinal tract, hypo- and hyper-activity of the central nervous system, Alzheimers, schizophrenia, migraines, obesity and the like diseases.

In yet another embodiment, the present invention discloses methods for preparing pharmaceutical compositions comprising the inventive imidazole compounds as an active ingredient. In the pharmaceutical compositions and methods of the present invention, the active ingredients will typically be administered in admixture with suitable carrier materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like, and consistent with conventional pharmaceutical practices. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Powders and tablets may be comprised of from about 5 to about 95 percent inventive composition.

Suitable binders include starch, gelatin, natural sugars, corn sweeteners, natural and synthetic gums such as acacia, sodium alginate, carboxymethylcellulose, polyethylene glycol and waxes. Among the lubricants there may be mentioned for use in these dosage forms, boric acid, sodium benzoate, sodium acetate, sodium chloride, and the like. Disintegrants include starch, methylcellulose, guar gum and the like. Sweetening and flavoring agents and preservatives may also be included where appropriate. Some of the terms noted above, namely disintegrants, diluents, lubricants, binders and the like, are discussed in more detail below.

Additionally, the compositions of the present invention may be formulated in sustained release form to provide the rate controlled release of any one or more of the components or active ingredients to optimize the therapeutic effects, i.e. antihistaminic activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. As an example may be mentioned water or water-propylene glycol solutions for parenteral injections or addition of sweeteners and pacifiers for oral solutions, suspensions and emulsions. Liquid form preparations may also include solutions or intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active components, e.g., an effective amount to achieve the desired purpose.

The quantity of the inventive active composition in a unit dose of preparation may be generally varied or adjusted from about 1.0 milligram to about 1,000 milligrams, preferably from about 1.0 to about 950 milligrams, more preferably from about 1.0 to about 500 milligrams, and typically from about 1 to about 250 milligrams, according to the particular application. The actual dosage employed may be varied depending upon the patient's age, sex, weight and severity of the condition being treated. Such techniques are well known to those skilled in the art.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

Capsule—refers to a special container or enclosure made of methyl cellulose, polyvinyl alcohols, or denatured gelatins or starch for holding or containing compositions comprising the active ingredients. Hard shell capsules are typically made of blends of relatively high gel strength bone and pork skin gelatins. The capsule itself may contain small amounts of dyes, opaquing agents, plasticizers and preservatives.

Tablet—refers to a compressed or molded solid dosage form containing the active ingredients with suitable diluents. The tablet can be prepared by compression of mixtures or granulations obtained by wet granulation, dry granulation or by compaction.

Oral gels—refers to the active ingredients dispersed or solubilized in a hydrophillic semi-solid matrix.

Powders for constitution refers to powder blends containing the active ingredients and suitable diluents which can be suspended in water or juices.

Diluent—refers to substances that usually make up the major portion of the composition or dosage form. Suitable diluents include sugars such as lactose, sucrose, mannitol and sorbitol; starches derived from wheat, corn, rice and potato; and celluloses such as microcrystalline cellulose. The amount of diluent in the composition can range from about 10 to about 90% by weight of the total composition, preferably from about 25 to about 75%, more preferably from about 30 to about 60% by weight, even more preferably from about 12 to about 60%.

Disintegrants—refers to materials added to the composition to help it break apart (disintegrate) and release the medicaments. Suitable disintegrants include starches; "cold water soluble" modified starches such as sodium carboxymethyl starch; natural and synthetic gums such as locust bean, karaya, guar, tragacanth and agar; cellulose derivatives such as methylcellulose and sodium carboxymethylcellulose; microcrystalline celluloses and cross-linked microcrystalline celluloses such as sodium croscarmellose; alginates such as alginic acid and sodium alginate; clays such as bentonites; and effervescent mixtures. The amount of disintegrant in the composition can range from about 2 to about 15% by weight of the composition, more preferably from about 4 to about 10% by weight.

Binders—refers to substances that bind or "glue" powders together and make them cohesive by forming granules, thus serving as the "adhesive" in the formulation. Binders add cohesive strength already available in the diluent or bulking agent. Suitable binders include sugars such as sucrose; starches derived from wheat, corn rice and potato; natural gums such as acacia, gelatin and tragacanth; derivatives of seaweed such as alginic acid, sodium alginate and ammonium calcium alginate; cellulosic materials such as methylcellulose and sodium carboxymethylcellulose and hydroxypropylmethylcellulose; polyvinylpyrrolidone; and inorganics such as magnesium aluminum silicate. The amount of binder in the composition can range from about 2 to about 20% by weight of the composition, more preferably from about 3 to about 10% by weight, even more preferably from about 3 to about 6% by weight.

Lubricant—refers to a substance added to the dosage form to enable the tablet, granules, etc. after it has been compressed, to release from the mold or die by reducing friction or wear. Suitable lubricants include metallic stearates such as magnesium stearate, calcium stearate or potassium stearate; stearic acid; high melting point waxes; and water soluble lubricants such as sodium chloride, sodium benzoate, sodium acetate, sodium oleate, polyethylene glycols and d,l-leucine. Lubricants are usually added at the very last step before compression, since they must be present on the surfaces of the granules and in between them and the parts of the tablet press. The amount of lubricant in the composition can range from about 0.2 to about 5% by weight of the composition, preferably from about 0.5 to about 2%, more preferably from about 0.3 to about 1.5% by weight.

Glidents—materials that prevent caking and improve the flow characteristics of granulations, so that flow is smooth and uniform. Suitable glidents include silicon dioxide and talc. The amount of glident in the composition can range from about 0.1% to about 5% by weight of the total composition, preferably from about 0.5 to about 2% by weight.

Coloring agents—excipients that provide coloration to the composition or the dosage form. Such excipients can include food grade dyes and food grade dyes adsorbed onto a suitable adsorbent such as clay or aluminum oxide. The amount of the coloring agent can vary from about 0.1 to about 5% by weight of the composition, preferably from about 0.1 to about 1%.

Bioavailability—refers to the rate and extent to which the active drug ingredient or therapeutic moiety is absorbed into the systemic circulation from an administered dosage form as compared to a standard or control.

Conventional methods for preparing tablets are known. Such methods include dry methods such as direct compression and compression of granulation produced by compaction, or wet methods or other special procedures. Conventional methods for making other forms for administration such as, for example, capsules, suppositories and the like are also well known.

Another embodiment of the invention discloses use of the pharmaceutical compositions disclosed above for treatment of diseases such as, for example, allergy, inflammation, nasal congestion, hypertension, glaucoma, sleeping disorders, states of hyper- and hypo-motility of the gastrointestinal tract, hypo- and hyperactivity of the central nervous system, Alzheimers, schizophrenia, migraine, obesity and the like. The method comprises administering a therapeutically effective amount of the inventive pharmaceutical composition to a mammalian patient having such a disease or diseases and in need of such a treatment.

Those skilled in the art will realize that the term "upper airway" means the upper respiratory system- i.e., the nose, throat, and associated structures.

It will be apparent to those skilled in the art that many modifications, variations and alterations to the present disclosure, both to materials and methods, may be practiced. Such modifications, variations and alterations are intended to be within the spirit and scope of the present invention.

The following EXAMPLES are being provided to further illustrate the present invention. They are for illustrative purposes only; the scope of the invention is not to be considered limited in any way thereby.

EXAMPLES

Unless otherwise stated, the following abbreviations have the stated meanings in the Examples below:

DBU=1,8-diazabicyclo[5.4.0]undec-7-ene
DBN=1,5-diazabicyclo[4.3.0]non-5-ene
EDCl=1-(3-dimethylaminopropyl)-3-ethylcarbodiimide
HOBT=1-hydroxybenzotriazole
DCC=dicyclohexylcarbodiimide
Dibal-H=diisobutylaluminum hydride
LAH=lithium aluminum hydride
NaBH(OAc)$_3$=sodium triacetoxyborohydride
NABH$_4$=sodium borohydride
NaBH$_3$CN=sodium cyanoborohydride
LDA=lithium diisopropylamide
p-TsOH=p-toluenesulfonic acid
m-CPBA=m-Chloroperbenzoic acid
TMAD=N,N,N',N'-tetramethylazodicarboxamide
CSA=camphorsulfonic acid
NaHMDS=sodium hexamethyl disilylazide
HRMS=High Resolution Mass Spectrometry
HPLC=High Performance Liquid Chromatography
LRMS=Low Resolution Mass Spectrometry
nM=nanomolar
Ki=Inhibition Constant for substrate/receptor complex
pA2=-logEC$_{50}$, as defined by J. Hey, *Eur. J. Pharmacol.*, (1995), Vol. 294, 329–335.
Ci/mmol=Curie/mmol (a measure of specific activity)
Tr=Triphenylmethyl
Tris=Tris(hydroxymethyl)aminomethane

I. GENERAL SYNTHETIC METHOD 'A': REDUCTIVE AMINATION

I. General Method 'A': Reductive Amination

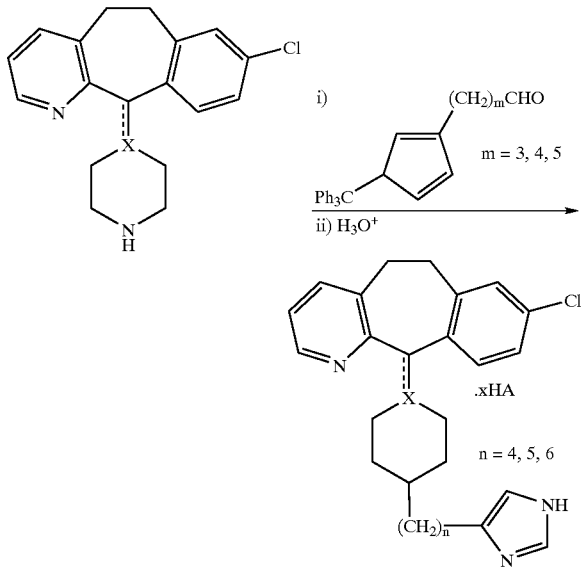

Example 1

Preparation of 1-(Triphenylmethyl)-1H-imidazol-4-carboxaldehyde (2)

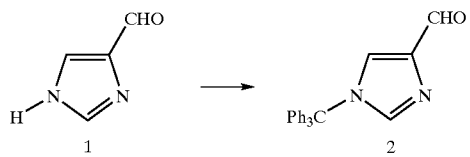

To a stirred suspension of aldehyde 1 (Aldrich Chemicals, Milwaukee, Wis.) (35.0 g; 0.364 mol) and triethylamine (55.8 mL; 0.400 mol) in dichloromethane (2 L), was added a solution of triphenylmethyl chloride in dichloromethane (600 mL) while maintaining the reaction temperature at approximately 15° C. with a cooling bath. The resultant solution was allowed to warm to room temperature and stirred for 19 h. The solution was washed with a solution of saturated brine and water (1:3.5; 3×600 mL), followed by brine (1×800 mL). It was dried over sodium sulfate; filtered to remove drying agent; and solvent removed under vacuum to obtain the desired tritylated product as an off-white solid, mp 186.5–194° C. [Trituration of this product with ether yielded a cream-colored powder with mp 195–197° C.]

Example 2

Preparation of 4-[(Z)-4-(Phenylmethoxy)-1-butenyl]-1-(triphenylmethyl)-1H-imidazole (3)

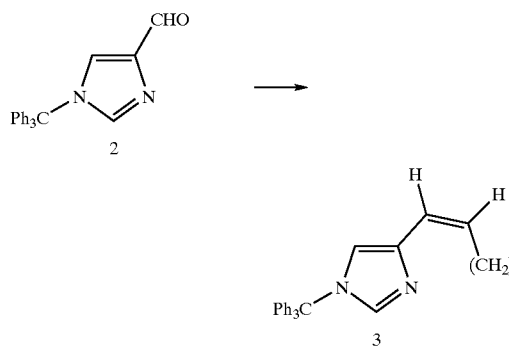

To a mechanically-stirred solution of aldehyde 2 in dry tetrahydrofuran (1 L), was added (3-benzyloxypropyl) triphenyl phosphonium bromide (30.02 g; 0.0611 mol). The resulting suspension was cooled to 15° C., and a 1.0 M solution (61.4 mL; 0.0614 mol) of potassium t-butoxide in tetrahydrofuran was added over 5 minutes. The reaction mixture was allowed to warm to room temperature and stirred for 2 h. The mixture was filtered through Celite; the filter was washed with tetrahydrofuran (2×150 mL); the filtrate and washings were combined and diluted with ether (800 mL); and refiltered through fresh Celite. The filtrate was concentrated under vacuum, and the residue was chromatographed on silica gel, eluting with a gradient of hexanes-ethyl acetate (3:1→2:1), to obtain the title compound as a pale yellow powder, mp 101–104° C. FABMS: 471 (MH$^+$; 6%); 243 (Ph$_3$C$^+$; 100%).

Example 3

Preparation of 1-(Triphenylmethyl)-1H-imidazole-4-butanol (4)

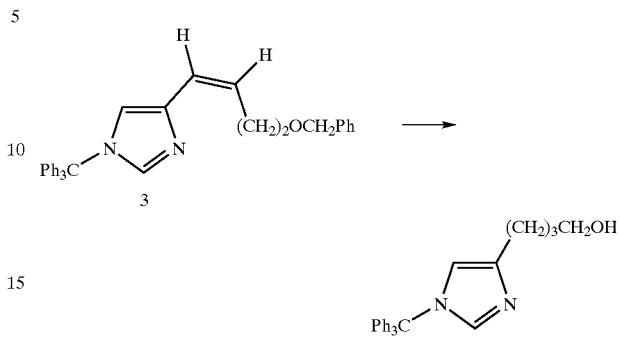

A mixture of the olefinic ether 3 (18.27 g; 0.0388 mol) in anhydrous methanol (350 mL), 1.0 M ethereal hydrochloric acid (38.8 mL; 0.0388 mol) and 10% palladium-on-carbon catalyst was hydrogenated at 48 psi for 30 min. on a Parr shaker. The reaction mixture was then filtered through Celite and washed the filter cake with methanol. The combined filtrate and washings were concentrated and dried under high vacuum to obtain the title alcohol hydrochloride as an off-white solid, mp 144–146° C.

Example 4

Preparation of ω-[1-(Triphenylmethyl)-1H-imidazol-4-yl]-butanal (5)

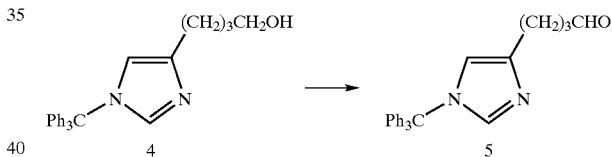

In a dry flask equipped to provide an inert gas atmosphere, a solution of oxalyl chloride (2.18 mL; 0.0250 mol) in dry dichloromethane (50 mL) was prepared and cooled to −60° C. in a CO$_2$-acetone bath. A solution of dimethylsulfoxide (3.60 mL; 0.0507 mol) in dry dichloromethane (10 mL) added dropwise over 5–10 min., while maintaining the reaction temperature at −55 to −60° C. It was stirred an additional 5 min at −60° C.; then a solution of alcohol hydrochloride (4) (8.67 g; 0.0207 mol) in dry dichloromethane (140 mL) was added over 15–20 minutes, maintaining reaction temperature in the range of −55 to −60° C. Stirring was continued at −60° C. for one hour; then neat triethylamine (17.6 mL; 0.126 mol) was added at a rate such that the reaction temperature was maintained at −55 to −60° C. The reaction was stirred for 5 min. at this temperature. The cooling bath was removed , and stirring continued at room temperature for 1.5 h. The reaction mixture was washed with water (4×50 mL), then with brine (75 mL); dried over anhydrous magnesium sulfate; and solvent was removed under vacuum to yield a viscous oil. To remove any remaining triethylamine hydrochloride, the residual oil was dissolved in diethyl ether (100 mL), washed with water (1×30 mL; 2×10 mL), then with brine (30 mL), and dried over anhydrous magnesium sulfate. Solvent was removed under vacuum to obtain the title aldehyde as a viscous yellow oil, sufficiently pure for further chemistry. FABMS: 381 (MH$^+$; 10%); 243 (Ph$_3$C$^+$; 100%).

Example 5

Preparation of Ethyl 5-[1-(Triphenylmethyl)-1H-imidazol-4-yl]4-Z-pentenoate

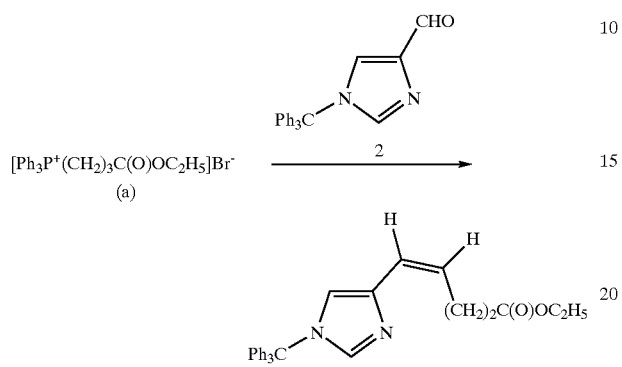

(i) Preparation of (ethoxycarbonylprop-1-yl) triphenylphosphonium bromide (a): A mixture of triphenylphosphine (24.6 g; 0.0936 mol) and ethyl 4-bromobutyrate (14.4 mL; 0.101 mol) was heated from room temperature to 105° C. over a period of 15–20 minutes, and heating of the resultant solution was continued at 105° C. for 10 minutes. The solution was allowed to cool, but while still warm, diethyl ether (50 mL) was cautiously added via a condenser. The resultant gum was triturated to obtain a white powder. The supernatant was decanted, fresh diethyl ether (50 mL) was added, and trituration continued for 10 min. The product was filtered, the cake was washed with diethyl ether; and solvent removed under vacuum from the combined filtrate and washings to obtain a mixture of oil and solids. This mixture was heated to 100° C., cautiously treated with diethyl ether (2×55 mL) and the trituration, filtration, and concentration sequence described above were repeated. The two batches of white solids obtained from this process were combined, triturated with toluene (150 mL) and filtered. The collected solids were washed with toluene and dried under high vacuum to obtain the title salt, mp 177–179° C. FABMS: 377 (M$^+$ for cation; 84%).

(ii) Preparation of ethyl 5-[1-(triphenylmethyl)-1H-imidazol-4-yl]4-Z-pentenoate: Under a nitrogen atmosphere, the triphenylphosphonium salt (a) (14.0 g; 0.0305 mol) was added to a stirred solution of aldehyde 2 (9.81 g; 0.029 mol) in tetrahydrofuran (500 mL). The resulting suspension was cooled to 0–5° C., 1M potassium t-butoxide in tetrahydrofuran (31 mL; 0.031 mol) was added over 3–5 min., and the mixture was stirred for 20 min. at 0–5° C. Celite was added to the reaction mixture, which was stirred briefly and filtered. The filter cake was washed with diethyl ether, followed by dichloromethane. The combined filtrate and washings were concentrated under vacuum. The residual oil was chromatographed on silica gel, and eluted with a gradient of hexanes-ethyl acetate (3:1→2:1), to obtain the title compound as a white solid, mp 90–92.5° C. FABMS: 437 (MH$^+$; 3%); 243 (Ph$_3$C$^+$; 100%).

Example 6

Preparation of 5-[1-(Triphenylmethyl)-1H-imidazol-4-yl]-4-Z-pentenal

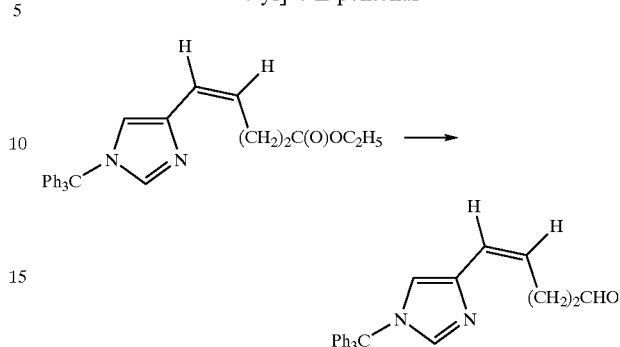

To a stirred solution of the ester (671 mg; 1.54 mmol) in dry dichloromethane (12 mL) contained in a cold bath, was added a 1.0M solution of DIBAL-H in toluene (3.08 mL; 3.08 mmol) over approximately 4 min., while maintaining the reaction temperature at −55 to −60° C. After 8–10 min. of stirring at −58° C., the reaction was quenched by the addition of methanol (0.4 mL) and water (6 mL). The reaction mixture was allowed to warm to room temperature. The gelatinous precipitate was removed by filtration through Celite. The filter cake was washed with dichloromethane, and the combined filtrate and washings were dried over anhydrous magnesium sulfate. The drying agent was filtered and solvent evaporated under reduced pressure to obtain the title aldehyde as a white powder, mp 117.5–120° C. FABMS: 393 (MH$^+$; 12%); 243 (Ph$_3$C$^+$; 100%).

Example 7

Preparation of -[1-(Triphenylmethyl)-1H-imidazol4-yl]-pentanal (6)

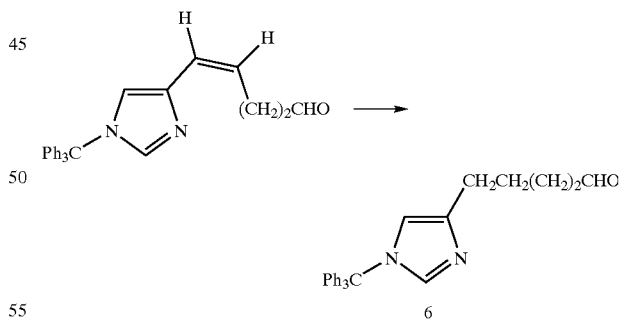

A mixture of the unsaturated aldehyde (5.42 g; 13.8 mmol) and 5% palladium-on-charcoal catalyst (0.50 g) in anhydrous methanol (130 mL) for 30 min. was hydrogenated at 30–35 psi on a Parr shaker. The catalyst was filtered through Celite, and the filtrate evaporated under reduced pressure. The residue was dried under high vacuum to obtain the title compound as a yellow viscous oil or glass sufficiently pure for further chemistry. FABMS: 395 (MH$^+$; 5%); 243 (Ph$_3$C$^+$; 100%).

Example 8

Preparation of Ethyl 6-[1-(Triphenylmethyl)-1H-imidazol-4-yl]-5-Z-hexenoate

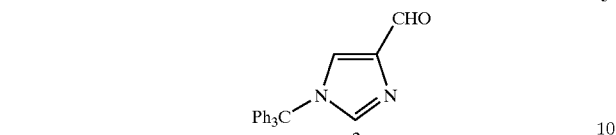
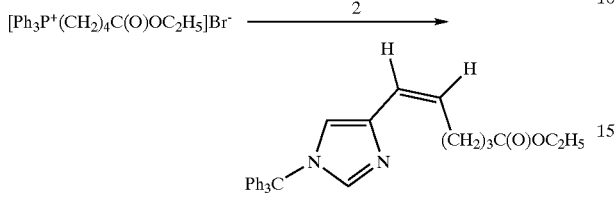

Under a nitrogen atmosphere, aldehyde 2 (12.4 g; 0.0367 mol) was added to a vigorously stirred partial suspension of 4-carboethoxybutyl triphenyl phosphonium bromide (from Lancaster Chemicals, Windham, N.H.) (20.2 g; 0.0408 mol) in tetrahydrofuran (630 mL). The suspension was stirred until aldehyde dissolved. The resultant mixture was cooled to 0–5° C. and 1M potassium t-butoxide in tetrahydrofuran (40.8 mL; 0.0408 mol) was added over 10 min., and the mixture stirred vigorously for 40 min. at 0–5 ° C., then for 30 min. at 5–10° C. Dry dichloromethane (100 mL) was added to dissolve any salt coating the walls of the flask, then the reaction mixture was allowed to warm to 20° C. Celite was added to the reaction mixture, which was stirred briefly, filtered and the filter cake was washed with dichloromethane. The combined filtrate and washings were concentrated under vacuum. The residual oil was chromatographed on silica gel, eluting with a gradient of hexanes-ethyl acetate (5:1→2:1), to obtain the title compound as a white powder, mp 78.5–85° C. FABMS: 451 (MH$^+$; 2%); 243 (Ph$_3$C$^+$; 100%).

Example 9

Preparation of 6-[1-(Triphenylmethyl)-1H-imidazol-4-yl]-5-Z-hexenal

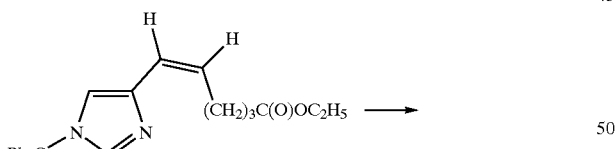
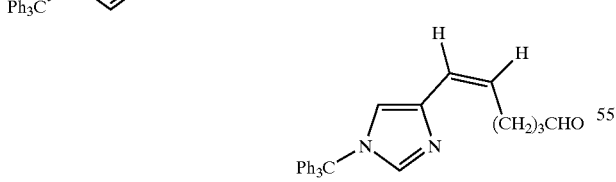

To a stirred solution of the title ester from Example 8 (3.98 g; 8.83 mmol) in dry dichloromethane (50 mL) contained in a cold bath, was added a 1.0M solution of DIBAL-H in toluene (17.7 mL; 17.7 mmol) over approximately 15 min., while maintaining the reaction temperature at −55 to −60° C. After 45 min. of stirring at −58 to −60° C., the reaction was quenched by the addition of methanol (2.3 mL) and water (34 mL). The reaction mixture was allowed to warm to room temperature and then was filtered through Celite. The filter cake was washed with dichloromethane, and the combined filtrate and washings were dried over anhydrous magnesium sulfate. The drying agent was filtered and solvent evaporated under reduced pressure to obtain the title aldehyde as a viscous oil sufficiently pure for use as described in Example 10. FABMS: 515 (impurity; 4%); 407 (MH$^+$; 2%); 243 (Ph$_3$C$^+$; 100%).

Example 10

Preparation of ω-[1-(Triphenylmethyl)-1H-imidazol-4-yl]-hexanal (7)

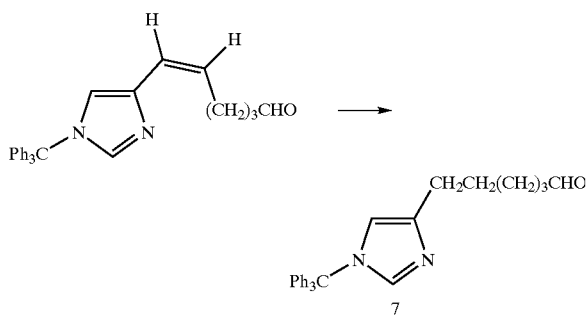

A mixture of the unsaturated aldehyde from Example 9 (3.41 g; 8.39 mmol) and 5% palladium-on-charcoal catalyst (0.3 g) in anhydrous methanol (50 mL) was hydrogenated for 45 min. at 30–35 psi on a Parr shaker. The catalyst was filtered through Celite, the filtrate evaporated under reduced pressure and the residual oil chromatographed on silica gel. Elution with a gradient of hexanes-ethyl acetate (2:1→1:1→1:2) yielded the title compound, which, after drying under high vacuum, was isolated as a white, slightly waxy hygroscopic solid, mp 78–80.5° C. FABMS: 451 (MH$^+$).

Example 11

Preparation of 1-(8-Chloro-6,11-dihydro-5H-benzo[5,6]cyclohepta[1,2-b]pyridin-11-yl)-4-[(1H-imidazol-4-yl)-methyl]-piperazine

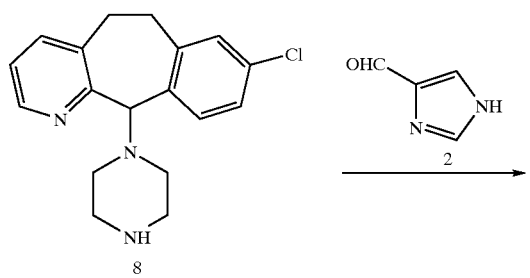

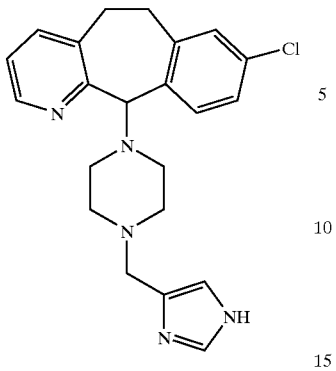

Example 12

Preparation of 8-Chloro-6,11-dihydro-11-[4-[4-(1H-imidazol4-yl)butyl]-1-piperazinyl]-5H-benzo[5,6]cyclohepta[1,2-b]pyridine

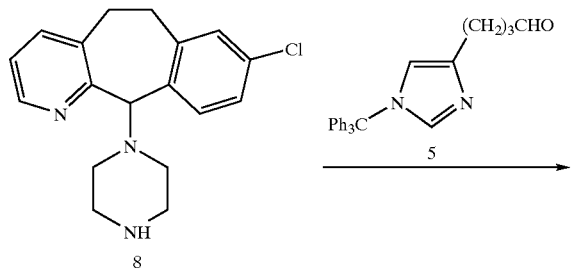

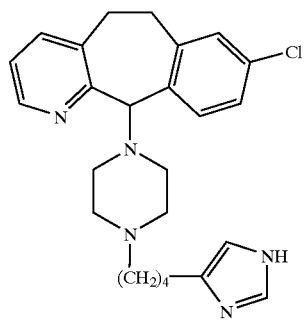

(i) To a stirred solution of 8-chloro-6,11-dihydro-11-(1-piperazinyl)-5H-benzo[5,6]cyclohepta[1,2-b]pyridine (8) (6.40 g; 0.020 mol) (disclosed in published application WO 95/10516, Apr. 20, 1995) and 1H-imidazol-4-carboxaldehyde (2) (1.96 g; 0.020 mol) in anhydrous methanol (100 mL), was added anhydrous magnesium sulfate (4.91 g). The resultant suspension was stirred at room temperature for 45 min. While maintaining the reaction temperature at 25–30° C. by use of a water bath, solid sodium cyanoborohydride (4.05 g of 95%; 0.0612 mol) was added and the resultant mixture allowed to stir at room temperature for 4 h. Another 0.64 g (0.0067 mol) of aldehyde 2 was added, and stirring was continued for another 16 h at room temperature. The reaction mixture was diluted with methanol (22 mL) and filtered. The filter cake was washed with methanol; the filtrate and washings were combined and solvent was removed under reduced pressure. The residue was dried under high vacuum to obtain an off-white glassy solid. This glass was redissolved in dichloromethane (175 mL)-methanol (30 mL), and washed with water (1×25 mL). The organic solution was dried over anhydrous magnesium sulfate, filtered, and solvent was removed under reduced pressure. The residue was chromatographed on silica gel, and eluting with a gradient of dichloromethane-methanol-concentrated ammonium hydroxide (95:5:0.1→90:10:0.1→85:15:0.1→80:20:0.1) yielded, after drying under high vacuum, the title compound as a white glass. FABMS: 394, 396 (MH$^+$; 100, 39%); 228 (67%).

(ii) To a stirred solution of the free base form of the title compound (5.48 g; 0.0139 mol) in methanol (200 mL), was added an ~3.4M solution (12.3 mL; 0.0417 mol) of ethereal hydrogen chloride. Solvent was removed under reduced pressure, and the residual solids were stirred with ether (150 mL). The solid was filtered, dried under a rubber dam, and redissolved in methanol (100 mL). The solution was treated with ~3.4M solution (10 mL; 0.034 mol) of ethereal hydrogen chloride. The solvent was removed under reduced pressure, the residual solids stirred with ether (150 mL). The solids were filtered, dried partially under a rubber dam, and then further dried under high-vacuum to obtain the hydrochloride salt of the title compound as a white powder that analyzed as a 2.8 hydrochloride hemihydrate, mp 190.5–192° C. (dec; darkens ~180° C.). $C_{22}H_{24}ClN_5$.2.8 HCl.0.5 $H_2O$. FABMS: 394, 396 (MH$^+$; 64/25%).

(i) To a stirred solution of 8-Chloro-6,11-dihydro-11-(1-piperazinyl)-5H-benzo[5,6]cyclohepta[1,2-b]pyridine (8) (348 mg; 1.11 mmol), ω-[1-(triphenylmethyl)-1H-imidazol-4-yl]-butanal (5) (459 mg; 1.21 mmol) and methanesulfonic acid (0.07 mL; 1.11 mmol) in anhydrous methanol (15 mL), was added anhydrous magnesium sulfate (267 mg). The resultant suspension was stirred at room temperature for 30 min. A 1.0M solution of sodium cyanoborohydride in tetrahydrofuran (0.78 mL; 0.78 mmol) was added and the resultant mixture allowed to stir at room temperature for 4.5 h. The mixture was filtered through Celite, and the filtrate evaporated under reduced pressure. The residue was dissolved in dichloromethane (20 mL) and washed successively with 1.1M sodium bicarbonate (10 mL), water (3×10 mL), and brine (15 mL). The organic layer was dried over anhydrous magnesium sulfate, filtered and solvent evaporated under reduced pressure. The gummy residue was chromatographed on silica gel, eluting with a gradient of dichloromethane-methanol-concentrated ammonium hydroxide (95:5:0.1→90:10:0.1), to obtain the imidazole-N-tritylated precursor of the title compound as a glassy solid. After drying under high vacuum, the product was subjected to detritylation without further treatment or characterization as below:

(ii) A methanol (75 mL) solution of the N-tritylated product (512 mg; 0.755 mmol) of the previous step and 1.0M hydrochloric acid in ether (8.7 mL; 8.7 mmol) were refluxed under a nitrogen atmosphere for 5 h. Solvent was removed under reduced pressure and the residue was triturated with ether. The mixture was filtered, and the collected solid washed with ether, and dried under high vacuum to obtain the HCl salt of the title compound as a white solid, mp 165–170° C. (dec). $C_{25}H_{30}ClN_5$.2.8 HCl.1.9 $H_2O$. FABMS: 436, 438 (MH$^+$; 49/18%).

By substituting respectively the homologous aldehydes 6 (from example 7) and 7 (from example 10) in the foregoing reaction processes, the following analogues of the title compound were prepared:

8-Chloro-6,11-dihydro-11-[4-[5-(1H-imidazol-4-yl)pentyl]-1-piperazinyl]-5H-benzo[5,6]cyclohepta[1,2-b]pyridine, trihydrochloride, 1.15 hydrate, 0.5 diethyl ether $C_{26}H_{32}ClN_5.3$ HCl 1.15 $H_2O.0.5$ $C_4H_{10}O$. FABMS: 450, 452 (MH$^+$; 100/35%).

8-Chloro-6,11-dihydro-11-[4-[6-(1H-imidazol-4-yl)hexyl]-1-piperazinyl]-5H-benzo[5,6]cyclohepta[1,2-b]pyridine, trihydrochloride, 0.5 hydrate, 0.5 methanolate $C_{27}H_{34}ClN_5.3$ HCl.0.5 $H_2O.0.5$ $CH_4O$. FABMS: 464, 466 (MH$^+$; 8/3%).

Example 13

Preparation of 8-chloro-6,11-dihydro-11-[1-[5-(1H-imidazol-4-yl)pentyl]-4-piperidinyl]-5H-benzo[5,6]cyclohepta[1,2-b]pyridine

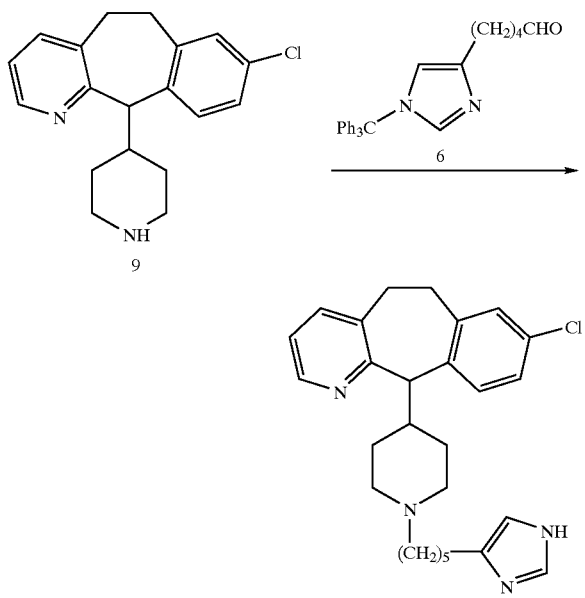

(i) To a stirred solution of 8-Chloro-6,11-dihydro-11-(4-piperidinyl)-5H-benzo[5,6]cyclohepta[1,2-b]pyridine (9) (499 mg; 1.59 mmol) (disclosed in published application WO 95/10516, Apr. 20, 1995), ω-[1-(triphenylmethyl)-1H-imidazol-4-yl]-pentanal (6) (699 mg; ~90% pure; 1.59 mmol) and methanesulfonic acid (0.10 mL; 1.59 mmol)) in anhydrous methanol (100 mL), was added anhydrous magnesium sulfate (380 mg) The resultant suspension was stirred at room temperature for 45 min. A 1.0M solution of sodium cyanoborohydride in tetrahydrofuran (1.12 mL; 1.12 mmol) was added and the resultant mixture stirred at room temperature for 22 h. The reaction mixture was filtered through Celite, and solvent evaporated under reduced pressure. The residue was dissolved in dichloromethane (25 mL) and washed successively with 1.1M sodium bicarbonate (15 mL) and water (2×10 mL). The organic layers were dried over anhydrous magnesium sulfate; filtered; solvent evaporated under reduced pressure and dried under high vacuum to obtain a pink glassy solid. The residual solid was chromatographed on silica gel, eluting with a gradient of 3.9M ammonia in methanol-dichloromethane (3:97→5:95), to obtain the imidazole-N-tritylated precursor of the title compound, which, after drying under high vacuum, was an off-white foam, mp 75–78° C. (melted to a viscous gum). FABMS: 451 (MH$^+$; 20%); 243 (Ph$_3$C$^+$; 100%).

(ii) A methanol (35 mL) solution of the N-tritylated product (426 mg; 0.675 mmol) from the previous step and 1.0M hydrochloric acid in ether (7.8 mL; 7.8 mmol) were refluxed under a nitrogen atmosphere for 12.5 h. The solvent was removed under reduced pressure and the residue partitioned between dichloromethane (25 mL) and 1.1M sodium bicarbonate solution (25 mL). The aqueous layer was extracted with dichloromethane (2×20 mL). The solvent was removed from the combined extracts to obtain a residual glass which was chromatographed on silica gel, eluting with a gradient of 3.9M ammonia in methanol-dichloromethane (5:95→10:90), to obtain the title compound, which, after drying under high vacuum, was a white powder, mp 65–68° C. (melted to a viscous gum). $C_{27}H_{33}ClN_4.1.5$ $H_2O$. CIMS: 449 (MH$^+$; 100%); 477 ([M+C$_2$H$_5$]$^+$; 24%).

(iii) To a stirred solution of the title compound (128 mg; 0.285 mmol) in methanol (5 mL), was added a 1.0M solution (1.0 mL; 1.0 mmol) of ethereal hydrogen chloride. Solvent was removed under reduced pressure, the residue dried under high-vacuum over phosphorus pentoxide, to obtain the trihydrochloride salt of the title compound as a white powder, mp 164–170° C. (dec to a viscous gum). $C_{27}H_{33}ClN_4.3$ HCl. $H_2O.0.5$ CH4O (MeOH). FABMS: 449 (MH$^+$; 55%).

By substituting the homologous aldehydes 5 (example 4) and 7 (example 10) in the foregoing reaction processes, the following analogues of the title compound were prepared:

8-Chloro-6,11-dihydro-11-[1-[4-(1H-imidazol-4-yl)butyl]-4-piperidinyl]-5H-benzo[5,6]cyclohepta[1,2-b]pyridine, trihydrochloride, 1.1 hydrate, mp 175–178° C. (dec). $C_{26}H_{31}ClN_4.3$ HCl.1.1 $H_2O$. FABMS: 435, 437 (MH$^+$; 7/2%).

8-Chloro-6,11-dihydro-11-[1-[6-(1H-imidazol-4-yl)hexyl]-4-piperidinyl]-5H-benzo[5,6]cyclohepta[1,2-b]pyridine, trihydrochloride, 1.5 hydrate. $C_{28}H_{35}ClN_4.3$ HCl.1.5 $H_2O$. FABMS: 463, 465 (MH$^+$; 100/44%).

Example 14

Preparation of 8-Chloro-6,11-dihydro-11-[1-[6-(1H-imidazol-4-yl)hexyl]-4-piperidinylidene]-5H-benzo[5,6]cyclohepta[1,2-b]pyridine

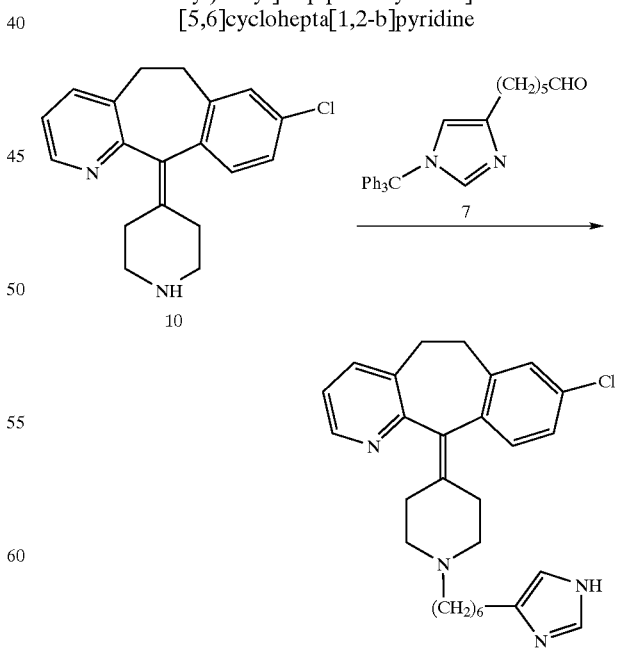

(i) To a stirred solution of 8-Chloro-6,11-dihydro-11-(4-piperidinylidene)-5H-benzo[5,6]cyclohepta[1,2-b]pyridine

(10) (284 mg; 0.914 mmol), (disclosed in published application WO 95/10516, Apr. 20, 1995), -[1-(triphenylmethyl)-1H-imidazol-4-yl]-hexanal (7) (393 mg; 0.962 mmol) and methanesulfonic acid (0.06 mL; 0.914 mmol)) in anhydrous methanol (10 mL), was added anhydrous magnesium sulfate (220 mg). The resultant suspension was stirred at room temperature for 30 min. A 1.0M solution of sodium cyanoborohydride in tetrahydrofuran (0.64 mL; 0.64 mmol) was added and the resultant mixture allowed to stir at room temperature for 23 h. The reaction mixture was filtered through Celite, and the filtrate evaporated under reduced pressure to obtain the mesylate salt of the imidazole-N-tritylated precursor of the title compound as a pink glass, which was detritylated without further purification. FABMS: 703 (MH$^+$; 35%); 243 (Ph$_3$C$^+$; 100%).

(ii) A methanol (10 mL) solution of the N-tritylated mesylate salt product (828 mg; 0.675 mmol) from the previous step and 1.0M hydrochloric acid in ether (10 mL; 10 mmol) were refluxed under a nitrogen atmosphere for 10 h. Solvent was removed under reduced pressure and the residue partitioned between dichloromethane (25 mL) and 1.1M sodium bicarbonate solution (25 mL). The aqueous layer was extracted with dichloromethane (2×20 mL). The combined extracts were washed with water (3×20 mL), dried over anhydrous magnesium sulfate, filtered and solvent removed from the filtrate to obtain a yellow glass. This solid was chromatographed on silica gel, eluting with a gradient of 3.9M ammonia in methanol-dichloromethane (5:95→10:90), to obtain the title compound as a free base. FABMS: 461 (MH$^+$; 11%).

(iii) To a stirred solution of the title compound (142 mg; 0.297 mmol) in methanol (3 mL), was added a 1.0M solution (1.0 mL; 1.0 mmol) of ethereal hydrogen chloride. Solvent was removed under reduced pressure, and the residue dried under high-vacuum over phosphorus pentoxide to obtain the trihydrochloride salt of the title compound as a light pink powder. $C_{28}H_{33}ClN_4$.3 HCl.0.6 H$_2$O.0.5 CH4O (MeOH). FABMS: 461 (MH$^+$; 100%).

By substituting the homologous aldehydes 5 (example 4) and 6 (example 7) in the foregoing reaction processes, the following analogues of the title compound were prepared:

8-Chloro-6,11-dihydro-11-[1-[4-(1H-imidazol-4-yl)butyl]-4-piperidinylidene]-5H-benzo[5,6]cyclohepta[1,2-b]pyridine, 2.8 hydrochloride, dihydrate, mp 162–165° C. (dec). $C_{26}H_{29}ClN_4$.2.8 HCl.2 H$_2$O. CIMS: 433, 435 (MH$^+$; 100/36%); 461, 463 ([M+C2H5]$^+$; 16/6%).

8-Chloro-6,11-dihydro-11-[1-[5-(1H-imidazol-4-yl)pentyl]-4-piperidinylidene]-5H-benzo[5,6]cyclohepta[1,2-b]pyridine, 2.9 hydrochloride, 0.5 methanolate. $C_{27}H_{31}ClN_4$.2.9 HCl.0.5 CH$_4$O (MeOH). FABMS: 447 (MH$^+$; 100%).

Example 15

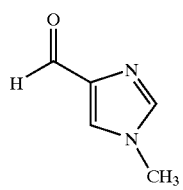

11

-continued

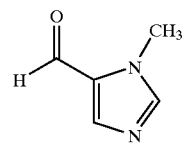

12

(i) Compounds (11) and (12) were prepared by reacting commercially available 4-imidazolecarboxaldehyde with CH$_3$I following known procedures.

By substituting analogous aldehydes (11) and (12), and reacting according to the procedure found in Example 12, the following compounds were prepared:

1-(8-Chloro-6,11-dihydro-5H-benzo[5,6]cyclohepta[1,2-b]pyridin-11-yl)-4-[(1-methyl-1H-imidazol-4-yl)-methyl]-piperazine, 4 hydrochloride. $C_{23}H_{26}ClN_5$. 4HCl and 1-(8-Chloro-6,11-dihydro-5H-benzo[5,6]cyclohepta[1,2-b]pyridin-11-yl)-4-[(1-methyl-1H-imidazol-4-yl)-methyl]-piperazine, 4 hydrochloride. $C_{23}H_{26}ClN_5$.4HCl.

Example 16

Preparation of 1-(8Chloro-6,11-dihydro-5H-benzo[5,6]cyclohepta[1,2-b]pyridin-11-yl)-4-[3-(1H-imidazol-4-yl)-1-oxo-propyl]piperazine(14)

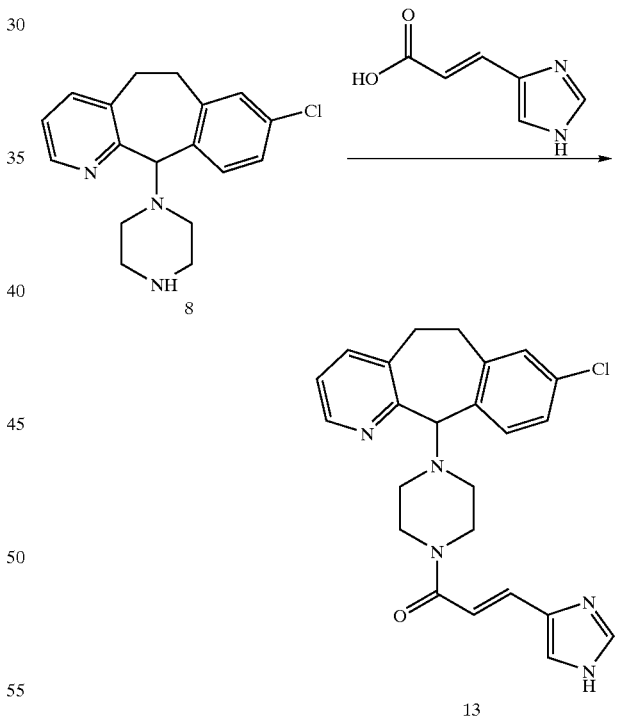

(i) Preparation of 1-(8-Chloro-6,11-dihydro-5H-benzo[5,6]cyclohepta[1,2-b]pyridin-11-yl)-4-[(E)-3-(1H-imidazol-4-yl)-1-oxo-2-propenyl]piperazine (13)

To a suspension of urocanic acid (1.38 g; 10.0 mmol) (from Aldrich Chemicals) in N,N-dimethylformamide (175 mL) under an inert atmosphere, was added 1-(3-dimethylaminopropyl)-3-ethylcarbodiimide hydrochloride (1.92 g; 10.0 mmol) and hydroxybenzotriazole (1.08 g; 8 mmol). The resultant mixture was warmed to 40° C. and stirring continued until all solids dissolved (~10 min.). To the resultant solution was added 8-chloro-6,11-dihydro-11-(1-piperazinyl)-5H-benzo[5,6]cyclohepta[1,2-b]pyridine (8) (2.51 g; 8.0 mmol), and the resultant solution was allowed to stir at room temperature for 18.5 h. Then water (250 microliters; 13.9 mmol) was added, and the solution was stirred briefly before concentrating under reduced pressure. The residual oil was partitioned between dichloromethane (100 mL) and water (100 mL). The organic extract was dried by filtration through anhydrous magnesium sulfate and solvent removed under reduced pressure. The residue was chromatographed on silica gel, eluting with dichloromethane-methanol-concentrated ammonium hydroxide (90:9:0.5), to obtain the title compound as a yellow powder that decomposed to a frothy gum at 160° C. SIMS: 434 (MH+; 50%).

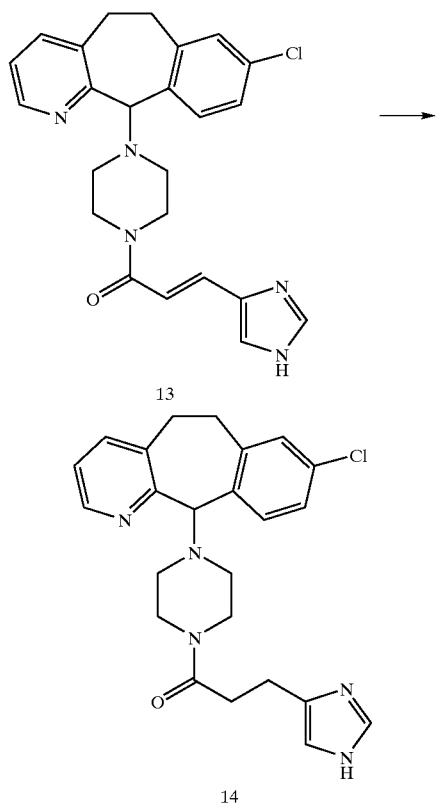

(ii) A mixture of unsaturated amide 13 (200 mg; 0.463 mmol) and 10% palladium-on-charcoal catalyst (40 mg) in anhydrous methanol (40 mL) was hydrogenated for 2.5 h. at 50 psi on a Parr shaker. A second portion (20 mg) of catalyst was added, and hydrogenation continued at 50 psi for a further 7 h. A third portion (20 mg) of catalyst was added and hydrogenation continued for a final 2 hours. The catalyst was filtered through Celite, solvent evaporated under reduced pressure and the residue dried under high vacuum to obtain the free base form of the title compound as a yellow powder. FABMS: 436 (MH+; 55%); 402 (8%); 228 (63%).

(iii) The free base form of the title compound (155 mg; 0.356 mmol) was dissolved in a mixture of dichloromethane (0.75 mL) and diethyl ether (0.75 mL). The cloudy solution was filtered through a syringe filter (0.45 micron), and the filtrate was treated with 1.0M ethereal hydrochloric acid (1.8 mL; 1.8 mmol). The hygroscopic precipitate that formed was crystallized from methanol-ethyl acetate to obtain the salt of the title compound as a white powder that decomposed at 165.5° C. and analyzed as $C_{24}H_{26}ClN_5O.2.35$ HCl.2.2 $H_2O.0.033$ $C_4H_8O_2$ (EtOAc). FABMS: 436 (MH+; 100%); 434 (15%); 402 (13%); 228 (70%).

Example 17

4-(8-Chloro-5,6-dihydro-11H-benzo[5,6]cyclohepta[1,2-b]pyridin-11-ylidene)-1-[3-(1H-imidazol-4-yl)-1-oxopropyl]-piperidine (16)

(i) Preparation of 4-(8-Chloro-5,6-dihydro-11H-benzo[5,6]cyclohepta[1,2-b]pyridin-11-yl)4-[(E)-3-(1H-imidazol-4-yl)-1-oxo-2-propenyl]-piperidine (15)

To a solution of urocanic acid (from Aldrich Chemicals) (1.8 g; 12.9 mmole) in anhydrous N,N-dimethylformamide (65 ml) was added 8-Chloro-6,11-dihydro-11-(4-piperidinylidene)-5H-benzo[5,6]cyclohepta[1,2-b]pyridine (10) (4 g; 12.9 mmole), 1-(3-dimethylaminopropyl)-3-ethylcarbodiimide hydrochloride (2.15 g; 11.2 mmoles) and hydroxybenzotriazole (1.74 g; 12.9 mmoles). The reaction

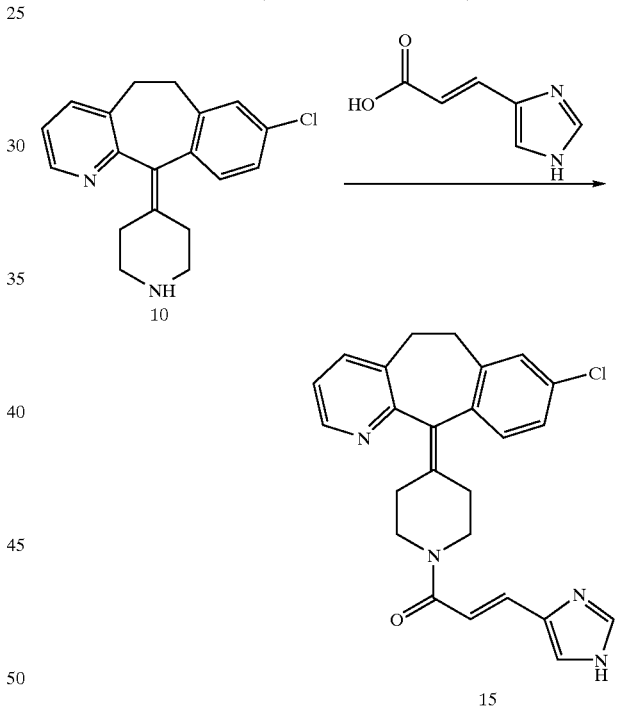

mixture was stirred for 48 hours at room temperature. Water was added, and it was then extracted with ethyl acetate several times. The organic layers were combined and washed with brine. The organics were dried over sodium sulfate and concentrated. The residue was purified by flash chromatography to give compound (15) (24%).

(ii) A mixture of unsaturated amide (15) (1.3 g; 3.0 mmoles) and 5% palladium-on-charcoal catalyst (1.3 g) in methanol (40 ml) was hydrogenated under a pressure of 60 psi at room temperature. The reaction was monitored by thin layer chromatography. When the starting material disappeared, the reaction of mixture was filtered through a bed celite, concentrated under reduced pressure

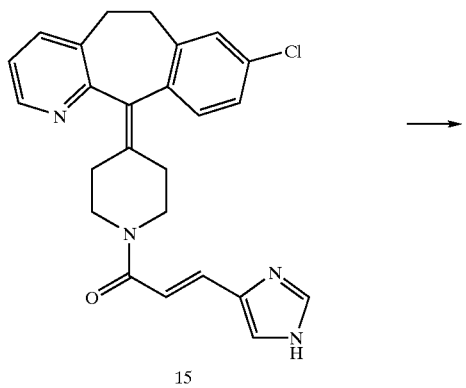

15

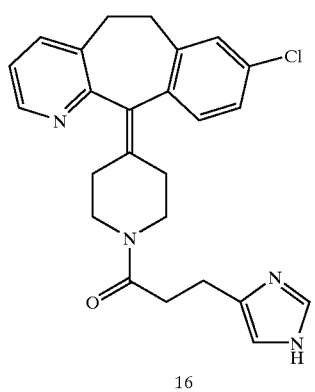

16 and purified by preparative thin layer chromatography to give the title compound (16), ($C_{25}H_{25}ClN_4O \cdot 2HCl \cdot 0.3C_4H_{10}O \cdot 2H_2O$) (54%).

Example 18

Preparation of 8-Chloro-5,6-dihydro-11-[1-[3-(1H-imidazol-4-yl)propyl]-4-piperidinylidene]-11H-benzo[5,6]cyclohepta[1,2-b]pyridine (17)

To a solution of compound (16) (0.65 g; 1.5 mmol) in anhydrous tetrahydrofuran (70 ml) was added a 1.0M solution of lithium aluminum hydride in tetrahydrofuran (4.6 ml; 4.6 mmol). The mixture was stirred at room temperature for 1.75 h. then diluted with ethyl ether and quenched with dropwise addition of saturated ammonium chloride solution. To saturated ammonium chloride

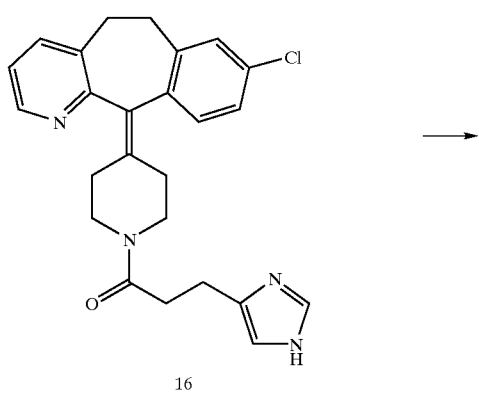

16

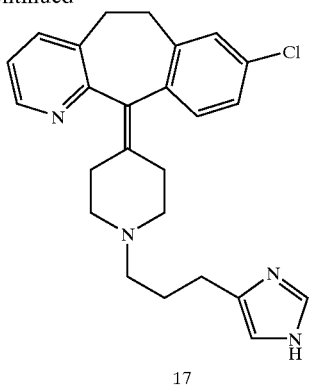

17 solution. To carbonate and then extracted with ethyl acetate. The combined organic extracts were dried over sodium sulfate, filtered and concentrated. Purifed by flash chromatography to give title compound (17) ($C_{25}H_{27}ClN_4 \cdot 3HCl \cdot 1.8 H_2O$) (79%).

Example 19

Preparation of 8-Chloro-6,11-dihydro-11-[4-[2-(1H-imidazol-4-yl)ethyl]-1-piperazinyl]-5H-benzo[5,6]cyclohepta[1,2-b]pyridine (i) To a solution of compound (8) (0.1 g; 0.32 mmole) in anhydrous dichloromethane (15 ml) cooled to 0° C. was added the trityl protected urocanic acid (0.14 g; 0.38 mmole), 1-(3-dimethylaminopropyl)-3-ethylcarbodiimide hydrochloride (0.092 g; 0.48 mmoles) and hydroxybenzotriazole (0.065 g; 0.48 mmoles). The reaction was stirred for 3 h. at room temperature, then quenched with saturated solution of sodium carbonate. The aqueous layer was extracted with ethyl acetate. The combined organic layers were then washed with brine,

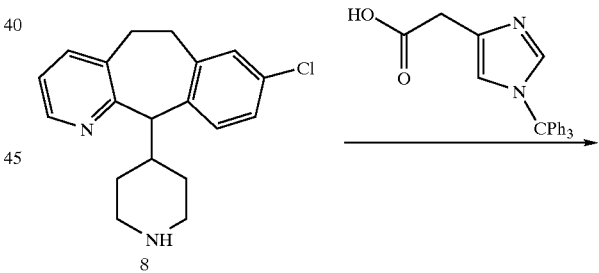

8

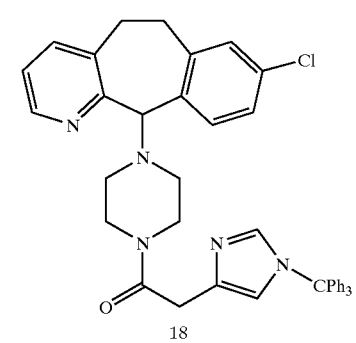

18 dried over potassium carbonate, filtered and concentrated. The product was purified by flash chromatography eluting with a gradient of 4M ammonia in methanol-dichloromethane (1:9–5:95) to afford compound (18) (77%).

(ii) To a solution of compound (18) (1.09 g; 1.6 mmole) in tetrahydrofuran (5 ml) was added a 1.0M solution of lithium aluminum hydride in tetrahydrofuran (4.8 ml; 4.8 mmole). The reaction stirred for 3 h. at room temperature, then was diluted with diethyl ether and quenched with saturated aqueous sodium sulfate. The solid was extracted with ethyl acetate. The combined organic layers were dried over potassium carbonate, filtered and concentrated. The residue was

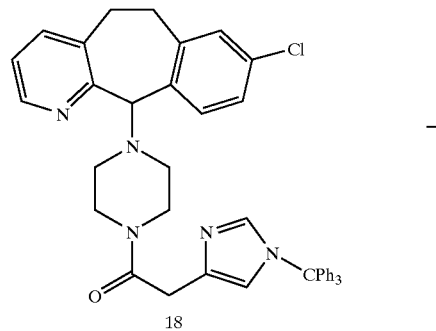

18

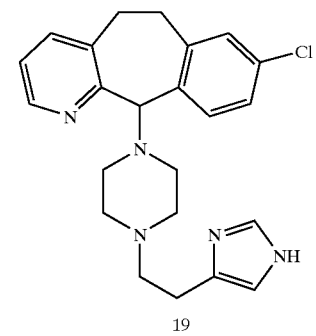

19 purified by flash chromatography eluting with a gradient of 4M ammonia in methanol-dichloromethane (1:9–5:95) (85%).

(iii) Using a similar procedure as in Example 12 the product from Step 2 was ditritylated to afford the HCl salt of the title compound as a white solid, ($C_{23}H_{26}ClN_5 \cdot 4$ HCl)

Example 20

Preparation of a Mixture of 4-(8-Chloro-6,11-dihydro-5H-benzo[5,6]cyclohepta[1,2-b]pyridin-11-yl)-1-[3-(1H-imidazol-4-yl)-1-oxopropyl]piperidine (21) and 4-(6,11-dihydro-5H-benzo[5,6]cyclohepta[1,2-b]pyridin-11-yl)-1-[3-(1H-imidazol-4-yl)-1-oxopropyl]piperidine (22)

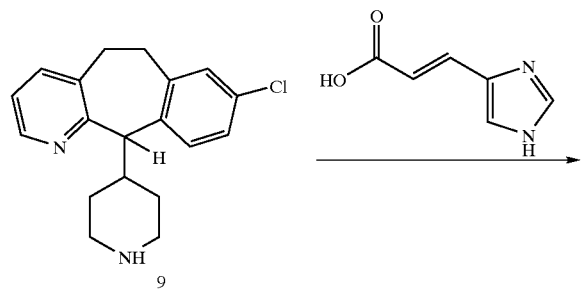

9

-continued

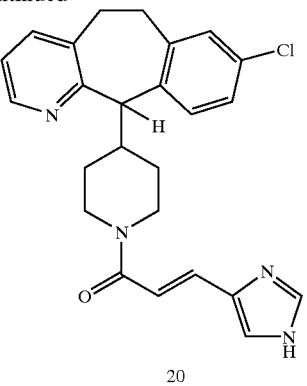

20

(i) Preparation of 4-(8-chloro-6, 11-dihydro-5H-benzo[5,6]cyclohepta[1,2-b]pyridin-11-yl)-1-[(E)-3-(1H-imidazol-4-yl)-1-oxo-2-propenyl]piperidine (20):

To a suspension of urocanic acid (258 mg; 1.87 mmol) in N,N-dimethylformamide (32.5 mL) under an inert atmosphere, was added 1-(3-dimethylaminopropyl)-3-ethylcarbodiimide hydrochloride (358 mg; 1.87 mmol) and hydroxybenzotriazole (201 mg; 1.49 mmol). The resultant mixture was warmed to 40° C., and stirring was continued until all solids dissolved (~10 min.). To the resultant solution was added 8-chloro-6,11-dihydro-11-(4-piperidinyl)-5H-benzo[5,6]cyclohepta[1,2-b]pyridine (9) (467 mg; 1.49 mmol), and the resultant solution was allowed to stir at room temperature for 17 h. Water (67 microliters; 3.7 mmol) was added, the solution was stirred briefly, and was then concentrated under reduced pressure. The residual oil was partitioned between dichloromethane (100 mL) and water (50 mL). It was treated with small volumes of methanol, and the resultant mixture was allowed to stand for 2 h. or as needed to obtain separation of the emulsified layers. The organic extract was dried by filtration through a pad of silica gel in a sintered glass funnel, eluting with dichloromethane-methanol-concentrated ammonium hydroxide (90:9:0.5). The solvent was removed from the filtrate under reduced pressure to obtain the title compound as a fluffy tan solid. CIMS: 433, 435 (MH$^+$; 100/47%); 461 ([M+$C_2H_5$]$^+$; 18%).

(ii) Preparation of a mixture of 4-(8-Chloro-6,11-dihydro-5H-benzo[5,6]cyclohepta[1,2-b]pyridin-11-yl)-1-[3-(1H-imidazol-4-yl)-1-oxopropyl]piperidine and 4-(6,11-dihydro-5H-benzo[5,6]cyclohepta[1,2-b]pyridin-11-yl)-1-[3-(1H-imidazol-4-yl)-1-oxopropyl]piperidine (21, 22):

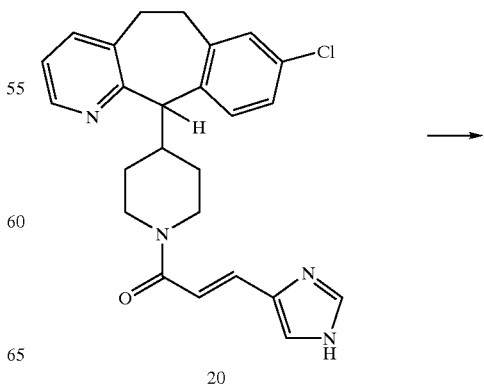

20

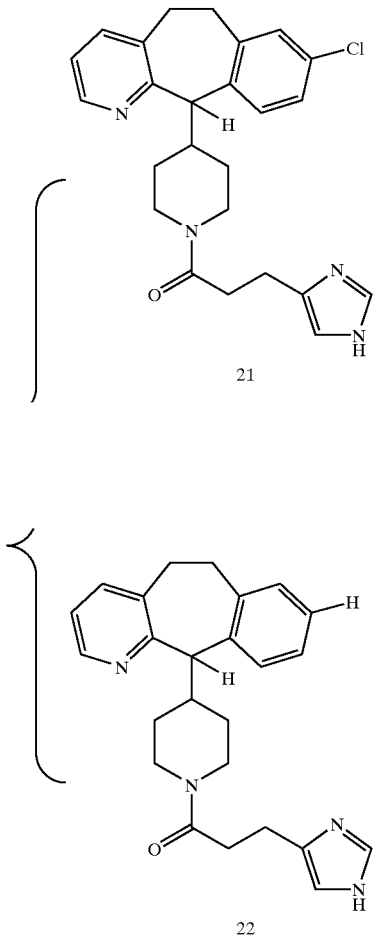

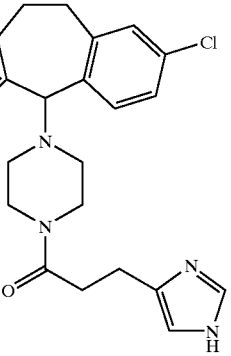

Example 21

Preparation of 1-(8-Chloro-6,11-dihydro-5H-benzo[5,6]cyclohepta[1,2-b]pyridin-11-yl)-4-[3-(1H-imidazol-4-yl)-propyl]piperazine (23)

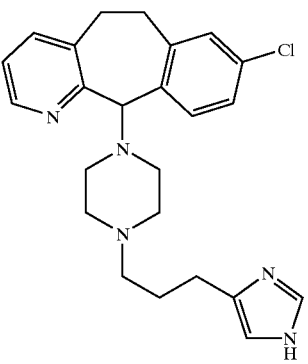

A mixture of unsaturated amide 20 (480 mg; 1.11 mmol), 1.0M ethereal hydrochloric acid (1.1 mL; 1.1 mmol) and 10% palladium-on-charcoal catalyst (216 mg) in anhydrous methanol (40 mL) was hydrogenated for 20 h. at 50 psi on a Parr shaker. The catalyst was filtered through Celite, the solvent evaporated under reduced pressure, and the residual solid partitioned between dichloromethane (30 mL) and saturated aqueous sodium bicarbonate (20 mL). The aqueous layer was extracted with dichloromethane (10 mL). The organic extracts were combined, washed with water (20 mL), followed by brine (20 mL) and dried by filtration through anhydrous sodium sulfate. Solvent was removed from the filtrate under reduced pressure, and the residue dried under high vacuum to obtain a fluffy white solid, which exhibited a homogeneous single spot with traces of minor impurities in a variety of TLC systems (varied proportions of dichloromethane-methanol-ammonium hydroxide). Spectroscopic and elemental analysis data revealed the product to be an approximately 2:1 mixture of the expected double bond reduction product ($M_1$) and its dechlorinated derivative ($M_2$). FABMS: 435, 437 ($M_1H^+$; 70/25%); 401 ($M_2H^+$; 100%). Spectroscopic and elemental analyses were in accord with the following formulas: $C_{25}H_{27}ClN_4O \cdot 0.5$ and $C_{25}H_{28}N_4O \cdot H_2O \cdot 0.125 \, CH_2Cl_2$.

(i) To a solution of 1-(8-chloro-6,11-dihydro-5H-benzo[5,6]cyclohepta[1,2-b]pyridin-11-yl)-4-[3-(1H-imidazol-4-yl)-1-oxo-propyl]piperazine(14) (310 mg; 0.711 mmol) in tetrahydrofuran (10 mL) stirred under an inert atmosphere, was added via syringe a 1.0M solution of lithium aluminum hydride in tetrahydrofuran (1.60 mL; 1.60 mmol) in small portions over approximately 3 min. The reaction solution was stirred at room temperature for 3 h. The reaction was quenched with vigorous stirring by the cautious, dropwise addition of water (61 microliters), followed successively by 15% aqueous sodium hydroxide (61 microliters) and water (183 microliters). The resultant precipitate was filtered, and solvent removed from the filtrate under reduced pressure. The residue was partitioned between dichloromethane (25 mL) and water (20 mL). The organic layer was washed with brine (20 mL); filtered through anhydrous sodium sulfate; and solvent removed from the filtrate to obtain the free base form of the title compound as a yellow powder. This was chromatographed on silica gel, eluting with dichloromethane-methanol-concentrated ammonium hydroxide (90:9:0.5), to obtain the title compound as an off-white powder that decomposed at ~91–98° C. CIMS: 422,424 ($MH^+$; 100/32%); 450, 452 ($[M+C_2H_5]^+$; 14/6%).

(ii) To a vigorously stirred solution of the above free base (66 mg; 0.152 mmol) in dichloromethane (2.75 mL), was added diethyl ether (8 mL), followed by 0.115M ethereal maleic acid (2.75 mL; 0.316 mmol). The resultant precipitate was triturated in the reaction medium for approximately 5 min. The supernatant was decanted, and fresh ether (15 mL) was added. This process was repeated twice more. The hygroscopic solid was then quickly filtered and dried under high vacuum over phosphorus pentoxide to obtain a maleate salt form of the title compound. FABMS: 422, 424 (MH$^+$; 86/31%); 228, 230 (53/19%). Spectroscopic and elemental analyses were in accord with the following formula: $C_{24}H_{28}ClN_5 \cdot 2\ C_4H_4O_4 \cdot 0.8\ H_2O \cdot 0.6\ C_4H_{10}O$ (Et$_2$O).

Example 22

Preparation of a Mixture of 8-Chloro-6,11-dihydro-11-[1-[3-(1H-imidazol-4-yl)propyl]-4-piperidinyl]-5H-benzo[5,6]cyclohepta[1,2-b]pyridine(24) and 6,11-dihydro-11-[1-[3-(1H-imidazol-4-yl)propyl]-4-piperidinyl]-5H-benzo[5,6]cyclohepta[1,2-b]pyridine (25)

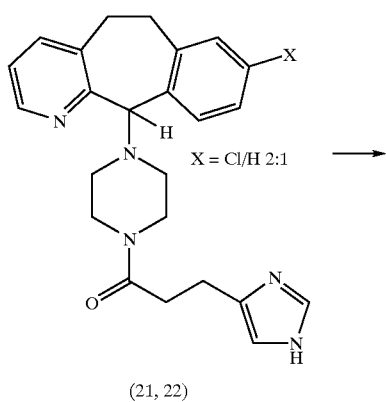

(21, 22)

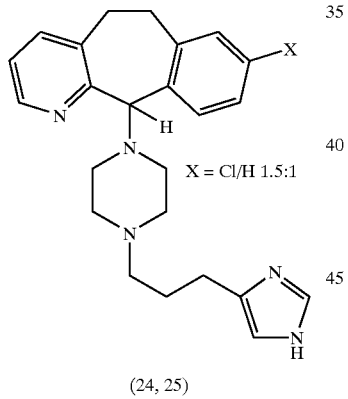

(24, 25)

(i) To a solution of the mixture of unsaturated amides (21,22) (275 mg; 0.414 mmol) in tetrahydrofuran (8 mL) stirred under an inert atmosphere, was added via syringe, a 1.0M solution of lithium aluminum hydride in tetrahydrofuran (1.28 mL; 1.28 mmol) in small portions over 3–4 min. The reaction was stirred at room temperature for 4 h. The vigorously stirred reaction was quenched by the cautious, dropwise addition of water (49 microliters), followed successively by 15% aqueous sodium hydroxide (49 microliters) and water (147 microliters). The resultant precipitate was filtered, and solvent removed from the filtrate under reduced pressure. The residue was partitioned between dichloromethane (20 mL) and water (20 mL). The organic layer was washed with brine (20 mL); filtered through anhydrous sodium sulfate; and solvent removed from the filtrate under reduced pressure. The residue was chromatographed on silica gel, eluting with dichloromethane-methanol-concentrated ammonium hydroxide (90:9:0.5), to obtain the free base form of the title mixture as a white powder. Spectroscopic and elemental analyses were in accord with the following formula: $C_{25}H_{29}ClN_4 \cdot 0.75\ C_{25}H_{30}N_4 \cdot 1.25\ H_2O$.

(ii) To a vigorously stirred solution of the above free base mixture (85 mg; ~0.203 mmol) in dichloromethane (1 mL), was added diethyl ether (3 mL), followed by 0.115M ethereal maleic acid (5.29 mL; 0.608 mmol). The resultant precipitate was triturated in the reaction medium for approximately 5 min. The supernatant was decanted, and fresh ether (3 mL) was added. This process was repeated twice more; then the hygroscopic solid was quickly filtered and dried under high vacuum to obtain the maleate salt form of the title mixture. Spectroscopic and elemental analysis data revealed the product to be an approximately 1.5:1 mixture of the chlorinated reduction product (M$_1$) and its dechlorinated derivative (M$_2$). FABMS: 421, 423 (M$_1$H$^+$; 65/29%); 387 (M$_2$H$^+$; 100%). Spectroscopic and elemental analyses were in accord with the following formula: $C_{25}H_{29}ClN_4 \cdot 0.68\ C_{25}H_{30}N_4 \cdot 3.6\ C_4H_4O_4 \cdot 4\ H_2O \cdot 0.5\ C_4H_{10}O$ (Et$_2$O).

Example 23

Preparation of 1-Trityl-4-chloromethyl imidazole

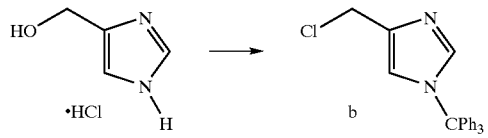

(i) Commercially available 4-hydroxymethyl imidazole hydrochloride (from Aldrich) and triphenyl methyl chloride were reacted according to literature procedure (Kelley, J. Med. Chem 20(5), 721, (1977).

(ii) The product from Example 23 (i) was suspended in benzene (464 ml) and azeotroped to dryness by distilling off 50 ml. of benzene. Then triethyl amine (27.76 ml) was added. The resultant mixture was cooled to zero degrees centigrade, and thionyl chloride was added dropwise over 10 minutes. After 35 minutes, ethyl acetate and water were added. The aqueous layer was separated and washed with ethyl acetate. The combined organic extracts were washed with saturated sodium bicarbonate then brine, dried over potassium carbonate, filtered and concentrated. Drying under high vacuum protected from light yielded the title compound (b).

Example 24

Preparation of 8-chloro-6,11-dihydro-11-[1-(1H-imidazol-4-ylmethyl)-4-piperidinyl]-5H-benzo[5,6]cyclohepta(1,2-b)pyridine (26)

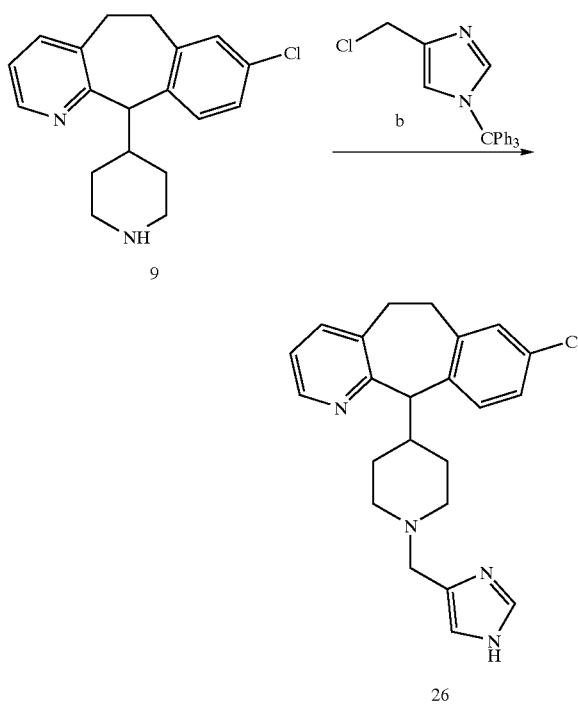

(i) To a solution of compound (9) (0.5 g; 1.9 mmole) in anhydrous dichloromethane (10 ml) was added the trityl protected imidazolechloride (b) from Example 23 (0.68 g; 1.9 mmole) and triethyl amine (0.264 ml; 1.9 mmole). The reaction was stirred overnight at room temperature. Water (10 ml) and ethyl acetate (20 ml) were added successively to the mixture. The aqueous layer was separated and then extracted with ethyl acetate (2×10 ml). The combined organic layers were dried over magnesium sulfate, filtered and concentrated. The residue was purified by flash chromatography (36%).

(ii) By using a similar procedure as in Example 12, the trityl precursor was deprotected to give the HCl salt of the title compound as a white solid (26), $C_{23}H_{25}ClN_4 \cdot 3HCl \cdot 1.5H_2O$.

By substituting compound (10) (Example 14) in the foregoing reaction process, the following compound was made: 8-chloro-6,11-dihydro-11-(1-(4-imidazolylmethyl)-4-piperidylidene)-5H-benzo[5,6]cyclohepta[1,2-b]pyridine, $C_{23}H_{23}ClN_4 \cdot 3$ HCl.

Example 25

Preparation of Compound (27)

This is disclosed in published application WO 95/10516.

Example 26

Preparation of Compound (28)

This is disclosed in U.S. Pat. No. 5,463,074.

Example 27

Preparation of 11-[4-[(1H-imidazol-4-yl)methyl]-1-piperidinyl]-8-chloro-6,11-dihydro-5H-benzo[5,6]cyclohepta[1,2-b]pyridine (29)

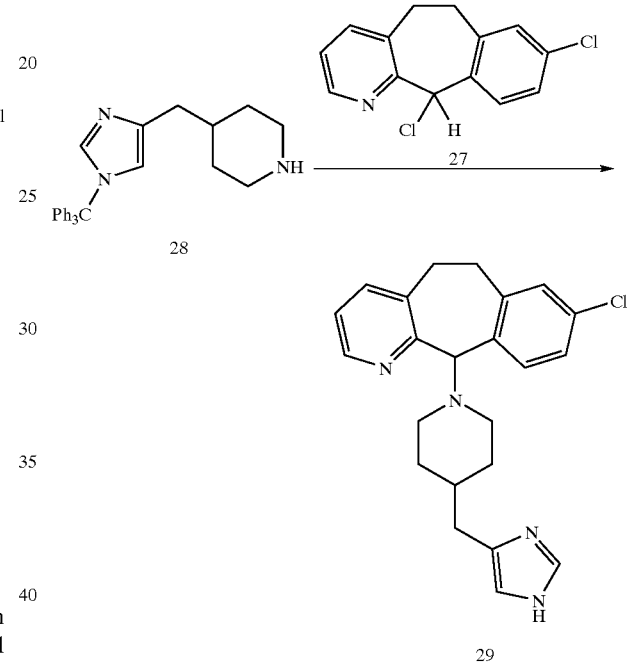

Compounds (27) and (28) were combined and reacted via the method reported in Example 24. The product was obtained as the HCl salt of the title compound (29), $C_{23}H_{25}ClN_4 \cdot 3$ HCl $\cdot 2$ $H_2O$ CIMS:393 (MH+)

Example 28

4-(1H-imidazol-4-yl)butyl 4-(8-chloro-6,11-dihydro-5H-benzo[5,6]cyclohepta[1,2-b]pyridin-11-yl)-1-piperazinecarboxylate (31)

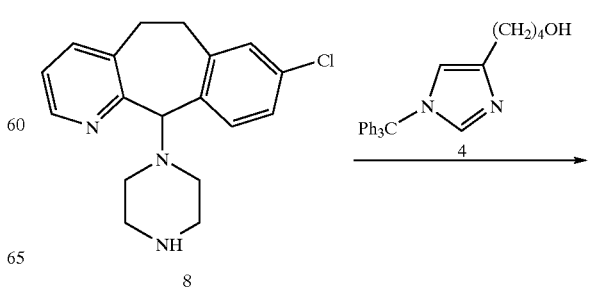

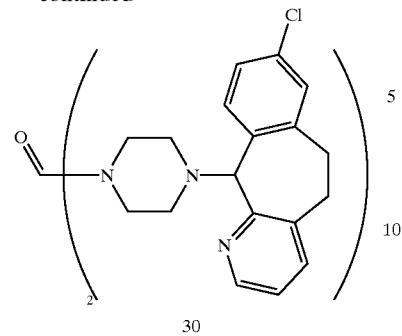

30

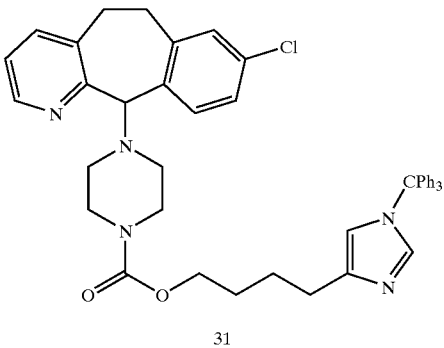

31

(i) To a stirred suspension of sodium hydride (200 mg of 60% dispersion; 5.0 mmol) in dry tetrahydrofuran (25 mL), was added portionwise alcohol hydrochloride (4) (1.05 g; 2.5 mmol) over a period of 10 min. The resultant suspension was stirred at room temperature for 3.5 h. The piperazine derivative (8) (706 mg; 2.25 mmol) was added, the mixture was diluted with dry tetrahydrofuran (25 mL), and the resultant suspension allowed to stir overnight at room temperature. Triethylamine (0.35 mL; 2.5 mmol) was added, followed by the addition over about 4 min. of a solution of triphosgene (252 mg; 0.849 mmol) in dry dichloromethane (2.5 mL) (mild exotherm). The resultant suspension was stirred at room temperature for 6 h; then the solids were filtered and washed with ethyl acetate. The filtrate and washings were combined, and solvent removed under reduced pressure. Chromatography of the residue on silica gel, eluting with a gradient of ethyl acetate-methanol (98:2→95:5), yielded the title tritylated product (31) as a white glassy foam. ESIMS: 722 (MH$^+$; 85%); 243 (Ph$_3$C$^+$; 100%). [A more polar fraction corresponding to symmetrical urea (30) was also isolated.]

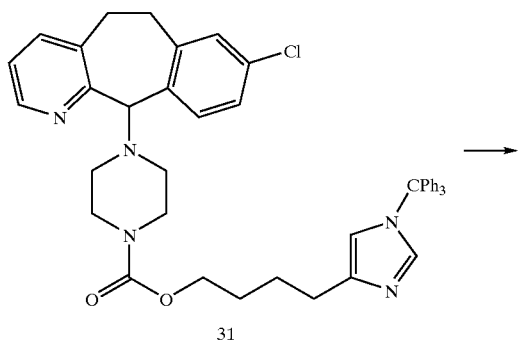

31

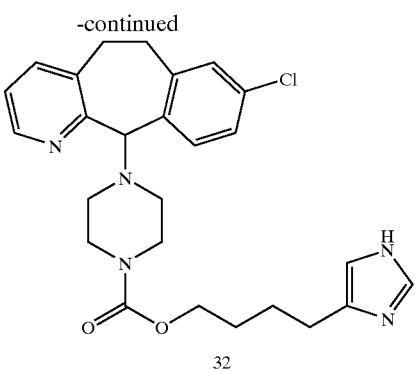

32

(ii) A mixture of the above tritylated carbamate (31) (310 mg; 0.430 mmol) and 15% aqueous hydrochloric acid (10 mL) in methanol (10 mL) was refluxed for 1.5 h. 6M HCl (4 mL) and methanol (1 mL) were added and reflux continued for another hour. Solvent was removed under reduced pressure. The residue was partitioned between dichloromethane (25 mL) and 1.1M aqueous sodium bicarbonate (13 mL). The aqueous layer was extracted with dichloromethane (3×25 mL), and the combined organic extracts were washed with water (2×) and brine. The organic layers were dried over anhydrous magnesium sulfate; drying agent was filtered, solvent removed under reduced pressure and the residue dried under high vacuum to obtain the title product (32) as a free base. FABMS: 460 (MH$^+$; 100%).

(iii) To a solution of the free base of the title product (98.4 mg; 0.205 mmol) in methanol (4.5 mL), was added 1.0M ethereal hydrochloric acid (0.72 mL; 0.72 mmol). The solvent was removed under reduced pressure, and the residue dried under high vacuum, over phosphorus pentoxide, to obtain the hydrochloride salt of the title product as a pale yellow foam. CIMS: 480 (MH$^+$; 97%); 251 (54%); 228 (100%). Spectroscopic and elemental analyses were in accord with the following formula: $C_{26}H_{30}ClN_5O_2 \cdot 2.6$ HCl$\cdot 4$ H$_2$O$\cdot 0.7$ CH$_4$O (MeOH).

Example 29

Preparation of (+)-(8-Chloro-6,11-dihydro-5H-benzo[5,6]cyclohepta[1,2-b]pyridin-11-yl)-4-[(1H-imidazol-4-yl)methyl]-piperazine(33) and (−)-(8-Chloro-6,11-dihydro-5H-benzo[5,6]cyclohepta[1,2-b]pyridin-11-yl)-4-[(1H-imidazol-4-yl)methyl]-piperazine (34)

(i) A hot (steam bath) mixture of the racemic piperazine compound (8) (1 g) in 8% aqueous acetonitrile (10 ml) was filtered leaving about 0.33 g residue. A hot solution of N-acetyl-L-leucine (0.55 g) in 8% aqueous acetonitrile (10 ml) was added to the filtrate followed by 8% aqueous acetonitrile (8 ml). The solution was allowed to stand and cool. After 24.5 h., the crystals were filtered and allowed to

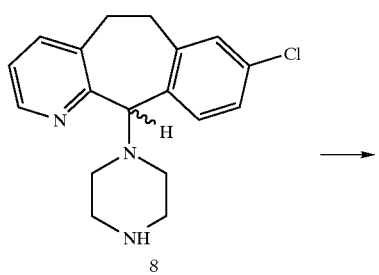

8

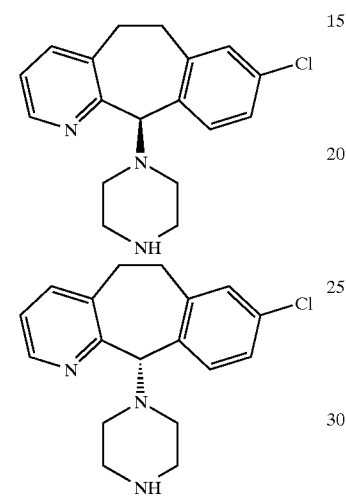

NH

Example 30

Preparation of 4-(8-Chloro-6,11-dihydro-5H-benzo[5,6]cyclohepta[1,2-b]pyridin-11-yl)-N-[4-(1H-imidazol-4-yl)butyl]-1-piperazinecarboxamide(36)

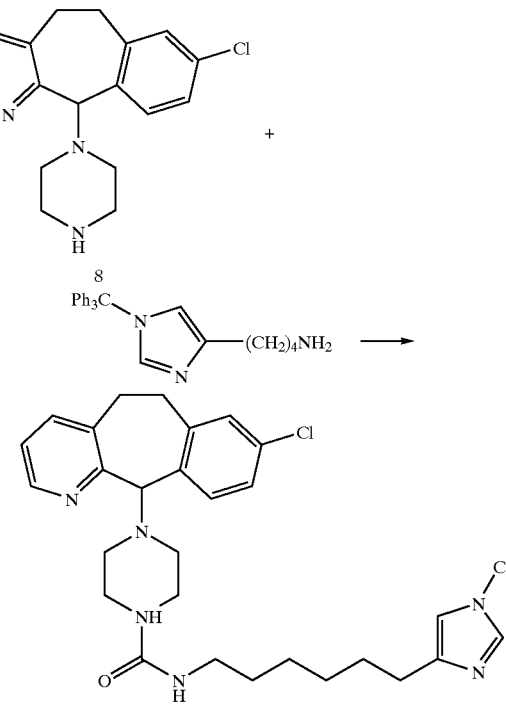

dry. The crystals were then stirred with potassium carbonate (0.11 g; 0.8 mmole), water (10 ml) and dichloromethane (10 ml). The aqueous layer was separated and extracted with dichloromethane (5 ml). The combined extracts were washed with brine, dried over sodium sulfate, filtered and concentrated to a white foam. The procedure was repeated twice more with the original racemic mixture to afford a total of 0.59 g having 82–90% ee. This material was then recycled in the same manner to afford 0.13 g with 100% ee. The combined mother liquors were concentrated and basified as above, then treated in the same manner with N-acetyl-D-leucine twice to give 0.39 g with 100% ee of the opposite enantiomer.

(ii) By reacting the respective (+) and (−) enantiomers of compound (8) with the trityl protected chloroimidazole following the procedure found in Example 13, the following compounds were made:

(+)-(8-Chloro-6,11-dihydro-5H-benzo[5,6]cyclohepta[1,2-b]pyridin-11-yl)-4-[(1H-imidazol-4-yl)methyl]-piperazine, $C_{22}H_{24}ClN_5 \cdot 4HCl \cdot 3H_2O$ CIMS: 394 (MH+).

(−)-(8-Chloro-6,11-dihydro-5H-benzo[5,6]cyclohepta[1,2-b]pyridin-11-yl)-4-[(1H-imidazol-4-yl)methyl]-piperazine, $C_{22}H_{24}ClN_5 \cdot 4HCl \cdot 4 H_2O$ CIMS: 394 (MH+).

(i) A solution of compound 8 (47.7 mg; 0.152 mmol) and triethylamine (0.025 ml; 0.177 mmol) in $CH_2Cl_2$ (0.5 ml) was added dropwise over 10 minutes at 20° C. to a stirred solution of triphosgene (16.4 mg; 0.0555 mmol) in $CH_2Cl_2$ (0.4 ml). After stirring the reaction mixture for an additional 20 minutes at room temperature, a solution of the amine (literature compound: Wolin, R. et al, Bioorg. Med. Chem. Lett. 8 (1998) 2157–162.) (57.2 mg; 0.15 mmol) and triethylamine (0.015 ml; 0.177 mmol) in dichloromethane (0.5 ml) was added dropwise over 7 minutes at 20° C. The yellow-green reaction was stirred at room temperature for 20.5 h. The crude reaction mixture was loaded on silica gel and chromatographed, eluting with a gradient of ethyl acetate-methanol (95:5→90:10), to obtain the tritylated product as a solid (35). FABMS:721 (MH+).

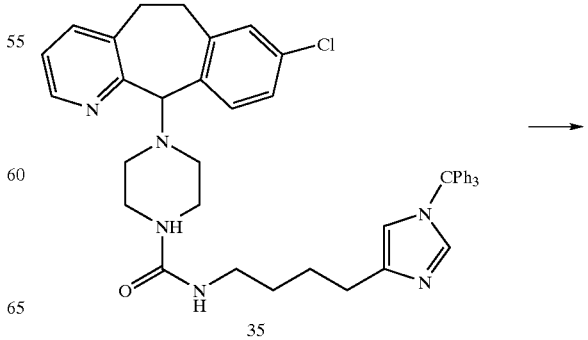

35

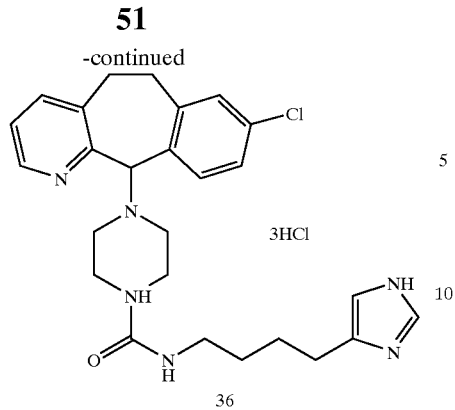

36

(ii) By using a similar procedure as in Example 12, the trityl precursor was deprotected to give the HCl salt of the title compound (36) as a light tan solid. FABMS:479 (MH$^+$). HRMS: ($C_{26}H_{32}ClN_6O$) calc. 479.2326, meas. 479.2320.

General Procedure for H1-Receptor Binding Assay

The procedure used was based on that disclosed in V.T. Tran et al, "Histamine $H_1$ receptors identified in mammalian brain membranes with [H-3]mepyramine", *Proc. Natl. Acad. Sci. U.S.A.* 75 (1978) 6290–6294.

I. Tissue Preparation Protocol for Histamine $H_1$ Receptor Binding Assay:
1. The tissue source was male Sprague-Dawley rat brain. These were purchased, stripped and frozen (available from Rockland Corporation, Gilbertsville, Pa.). The buffer used was ice-cold 50 mM Tris-HCl, pH 7.5. (The pH was determined at 25° C.)
2. The brains were spread out on plastic wrap on the benchtop and allowed to thaw for 10–15 min. After this, everything was kept ice-cold.
3. Two brains were put in each 50 ml round bottom centrifuge tube and 25 ml of buffer was added. Then they were broken up with a Polytron (from Brinkmann Instruments, Westbury, N.Y.) equipped with a PT-10 tip at setting 6 for 30 sec.
4. The volume in the tube was brought up to 45 ml and mixed and the particulate material was centrifuged at 1000×g (3000 rpm, SS-34 rotor) for 10 min to remove nuclei and unbroken cells.
5. Pellets were discarded and the supernatants were centrifuged 10 min at 50,000×g (20,000 rpm, SS-34 rotor).
6. The high-speed pellets were resuspended in a volume of Tris buffer equal to the original (4 ml), the contents of all tubes were pooled, and a sample was taken for BCA protein assay. The material was aliquotted, 45 ml per round-bottom tube, and the resuspension was recentrifuged. The yield of protein was approximately 20 mg/brain, so there was about 40 mg of protein per tube.
7. Pellets were frozen at −80° C.

II. $H_1$ Histamine Receptor Binding Assay: Materials: 96-well, deep-well, polypropylene plates, [$^3$H] pyrilamine, 20–30 Ci/mmol, from Dupont NEN Life Science Products, Boston, Mass.), chlorpheniramine maleate (from Schering-Plough Corporation, Kenilworth, N.J.) as standard, stored as frozen $10^{-5}$, $10^{-6}$, $10^{-7}$, $10^{-8}$M solutions.
1. FDCL and comparative compounds for assay were independently solubilized at 1mg/ml DMSO by vortexing, or if necessary by sonication. The first dilution, 100-fold, was made in 50 mM Tris-HCl, pH 7.5, at room temperature. The three or four subsequent ten-fold serial dilutions were made in 1% DMSO/50 mM Tris-HCl, pH 7.5. Drug solutions and assay plates were kept at room temperature during the course of the assay set up.
2. Test compounds were assayed at four or five concentrations: 1, 0.1, 0.01, 0.001, and 0.0001 μg/ml. Twenty μl of drug solution was pipeted into each of three wells. A chlorpheniramine maleate standard was assayed at $10^{-9}$ to $10^{-6}$ M, 20 μl of each of the appropriate solutions being pipeted into triplicate wells. Total and nonspecific ($10^{-6}$ M chlorpheniramine maleate) binding were determined at least in quadruplicate. For total binding, 20 μl of buffer was pipeted and for nonspecific 20 μl of $10^{-5}$ M chlorpheniramine maleate was pipeted into each well.
3. [$^3$H]Pyrilamine was diluted approximately 2000-fold with ice-cold mM Tris-HCl, pH 7.5 (to a working concentration of 20–25 nM), and put on ice.
4. A frozen tissue pellet was thawed in a 25° C. water bath, resuspended in 50 mM Tris-HCl, pH 7.5, at 1.7–2 mg/ml by brief break-up on the Polytron, and put on ice.
5. Twenty μl of diluted [$^3$H]pyrilamine was added to each well.
6. One hundred fifty μl of tissue suspension was added to each well.
7. The top of the plate was covered and it was placed in a 25° C. shaking water bath (about 60 oscillations/min) for 30 min.
8. Samples were filtered on a Tomtec Mach 2 harvester (available from Tomtec Corporation, Orange, Conn.) through a GF/B filter mat (from Wallac, Inc., Gaithersburg, Md.) presoaked in 0.3% polyethylenimine. Each sample was thrice washed with ice-cold 50 mM Tris-HCl, pH 7.5 dried 20 sec on the Tomtec, and dried 3–4 min in a microwave oven on a paper towel. The filter was impregnated with MELTILEX brand wax scintillant (from Wallac Corporation) and counted on a Betaplate scintillation counter (from Wallac Corporation).
9. Specific binding was determined as the difference between total and nonspecific binding. The percent inhibition in the presence of inhibitor or standard was determined using the formula: [1-(sample binding-nonspecific binding)/specific binding]×100 For compounds that inhibit more than 50% at 1 μg/ml, an $IC_{50}$ value was interpolated from proximate concentrations. The value was converted to a nM value using the compound formula weight and a $K_i$ value was calculated using the equation of Cheng and Prusoff ($K_i=IC_{50}/(1+[L]/K_D)$, [Y-C. *Cheng and W. H. Prusoff*, "Relationship between the inhibitory constant ($K_i$) and the concentration of inhibitor which causes 50 per cent inhibition ($IC_{50}$) of an enzymatic reaction", *Biochem. Pharmacol.* 22 (1973) 3099–3108]. Lower value of $K_i$ indicates greater binding affinity.

General Procedure for $H_3$-Receptor Binding Assay

The source of the $H_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM [$^3$H]R-α-methyl histamine (8.8 Ci/mmol) or 3 nM [$^3$H]N$^α$-methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a K$_i$ (nM). The results are given in the Table 1 for the HCl salt of the indicated compound.

TABLE 1

| STRUCTURE | H$_3$ Ave Ki (nM) | H$_3$ % Inhibition | H$_1$ Ave Ki (nM) | H$_1$ % inhibition |
|---|---|---|---|---|
| 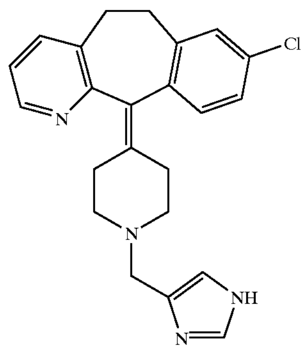 | 660 |  | 16 |  |
| Racemic | 150 |  | 36.8 |  |
| (+)-Isomer | 121 |  | 4.6 |  |

TABLE 1-continued
| STRUCTURE | H₃ Ave Ki (nM) | H₃ % Inhibition | H₁ Ave Ki (nM) | H₁ % inhibition |
|---|---|---|---|---|
| 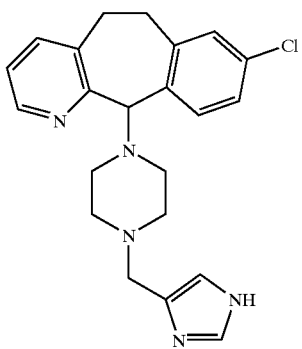 (−)-Isomer | 133 | | 15.4 | |
| 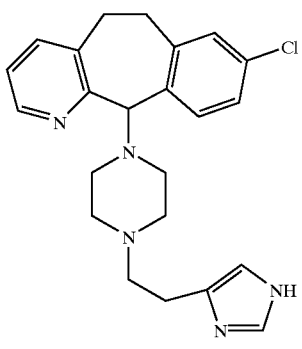 | 53 | | 5.6 | |
| 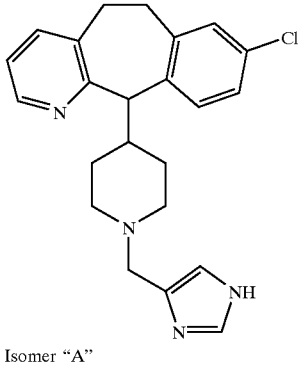 Isomer "A" | 15 | | 1.2 | |
| 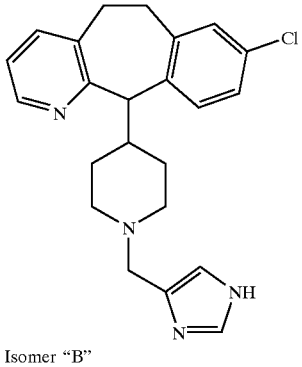 Isomer "B" | 91 | | 182 | |

TABLE 1-continued

| STRUCTURE | $H_3$ Ave Ki (nM) | $H_3$ % Inhibition | $H_1$ Ave Ki (nM) | $H_1$ % inhibition |
|---|---|---|---|---|
| (structure) | | 47 | | |
| (structure) | 260 | | 4.1 | |
| (structure) | 5 | | 24 | 84 |

TABLE 1-continued

| STRUCTURE | H₃ Ave Ki (nM) | H₃ % Inhibition | H₁ Ave Ki (nM) | H₁ % inhibition |
|---|---|---|---|---|
| (structure) | | 2 | 6 | 91 |
| (structure) | 18 | | 300 | 42 |
| (structure) | 68.5 | | 31.5 | |

TABLE 1-continued

| STRUCTURE | H₃ Ave Ki (nM) | H₃ % Inhibition | H₁ Ave Ki (nM) | H₁ % inhibition |
|---|---|---|---|---|
| 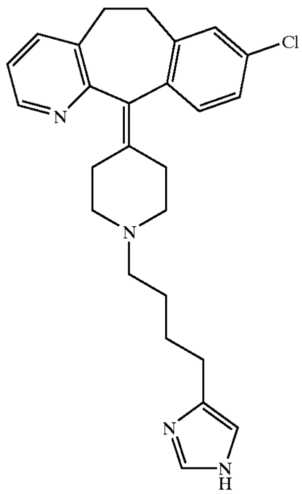 | 25.2 | | 10.5 | |
| | 44 | | 200 | |
| 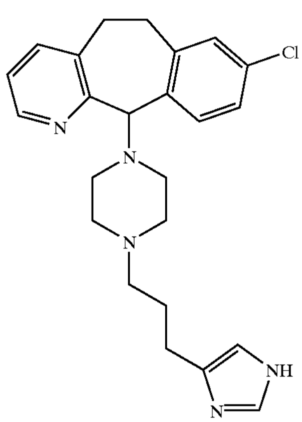 | 173 | | 7.5 | |

TABLE 1-continued

| STRUCTURE | H₃ Ave Ki (nM) | H₃ % Inhibition | H₁ Ave Ki (nM) | H₁ % inhibition |
|---|---|---|---|---|
| 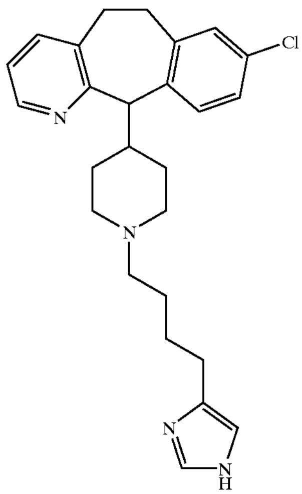 | 42 | | 14.3 | |
| 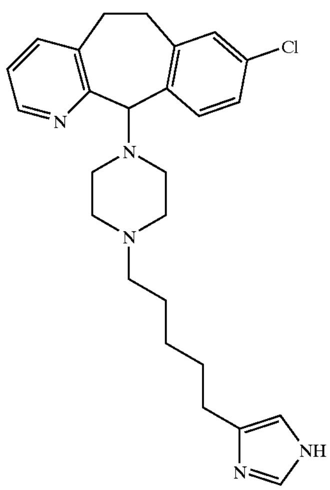 | 32 | | 12.5 | |
| 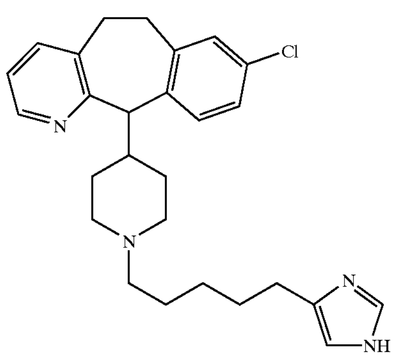 | 22.5 | | 7 | |

TABLE 1-continued
| STRUCTURE | $H_3$ Ave Ki (nM) | $H_3$ % Inhibition | $H_1$ Ave Ki (nM) | $H_1$ % inhibition |
|---|---|---|---|---|
| 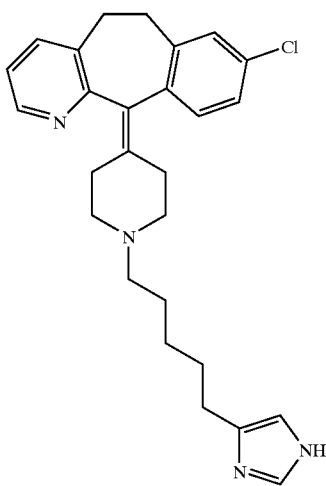 | 26.5 | | 2.5 | |
| 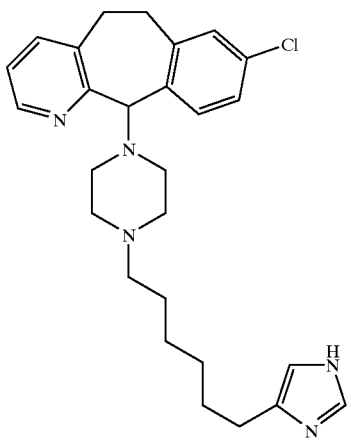 | 41 | | 8 | |
| 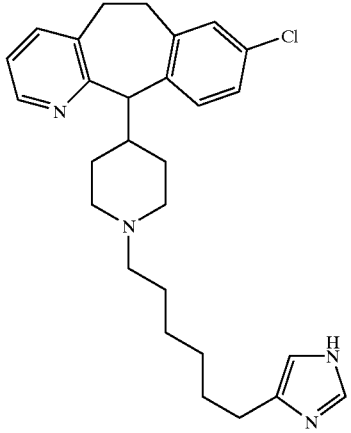 | 27.5 | | 5.5 | |

TABLE 1-continued

| STRUCTURE | H₃ Ave Ki (nM) | H₃ % Inhibition | H₁ Ave Ki (nM) | H₁ % inhibition |
|---|---|---|---|---|
| [structure] | 33.5 | | 12 | |
| [structure] | 148 | | 36 | |
| [structure] | 47 | | 250 | |

From these test results, it would be apparent to the skilled artisan that the compounds of the invention have utility in treating inflammation, allergy, diseases of the GI-tract, cardiovascular disease, nasal congestion, disturbances of the central nervous system and the like diseases stated earlier.

What is claimed is:

1. A compound, or enantiomers, stereoisomers and tautomers thereof, or pharmaceutically acceptable salts or solvates of said compound, said compound having the structure shown in Formula I:

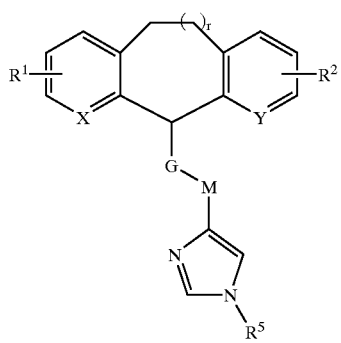

Formula I wherein:

X is N or N-oxide; y is CH; f=1;

G is a moiety selected from the group consisting of the moieties II, III and IV with the top end of said II, III and IV being linked to the tricyclic moiety and the bottom end of II, III and IV being linked to M:

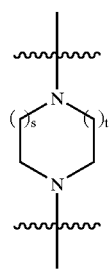

II

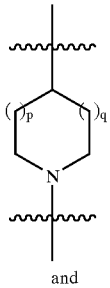

III and

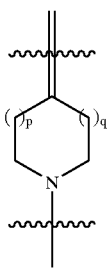

IV where s=t=1 or 2; and p=q=0, 1 or 2;

M is a moiety selected from the group consisting of $C_1$–$C_8$ alkyl; —C(O)—$(CH_2)_y$—; —$(CH_2)_x$—A—$(CH_2)_y$—; —C(O)—O—$(CH_2)_d$—; and —C(O)—$NR^3$—$(CH_2)_d$—; where A=O, $S(O)_r$—, and —$NR^4$—;

n=0, 1, 2 or 3;

x is a whole number in the range 2–5;

y is a whole number in the range 0–5;

d is a number in the range 0–5;

r=0, 1 or 2;

$R^1$ and $R^2$ may each number 1–3 and are independently selected from the group consisting of hydrogen, lower alkyl, lower alkoxy, halogen, $OCF_3$, $OCHF_2$, —OH, and —$N(R^4)_2$;

$R^3$ is selected from the group consisting of hydrogen, lower alkyl, and polyhaloloweralkyl;

$R^4$ is selected from hydrogen, lower alkyl, polyhalolower alkyl; and $R^5$ is H, $C_1$–$C_6$ alkyl or OH.

2. The compound of claim 1, wherein $R_1$ and $R_2$ are independently selected from H, halogen, hydroxy or lower alkoxy, and f is 1.

3. The compound of claim 2, wherein X is N and Y is CH.

4. The compound of claim 2, wherein G is:

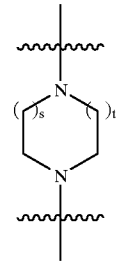

wherein s and t are as defined.

5. The compound of claim 2, wherein G is:

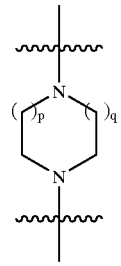

where p and q are as defined.

6. The compound of claim 2, wherein G is:

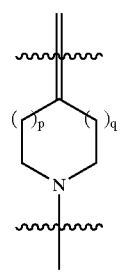

where p and q are as defined.

7. The compound of claim 4, wherein G is:

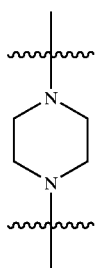

and M is an alkyl group containing 1–6 carbon atoms.

8. The compound of claim 6, wherein G is:

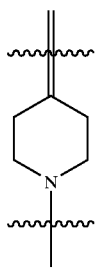

and M is an alkyl group containing 1–6 carbon atoms.

9. The compound of claim 1, where X is N, Y is CH, $R^1$ is H, $R^2$ is Cl, and $R^5$ is H.

10. The compound of claim 5, wherein p=q=1, and M is an alkyl group containing 1–6 carbon atoms.

11. The compound of claim 2, wherein M is —C(O)—$(CH_2)_g$—, wherein g is a number 0–3.

12. The compound of claim 2, wherein M is —C(O)—$NR^3$—$(CH_2)_d$—, wherein d is a number 0–5.

13. The compound of claim 1, wherein G is:

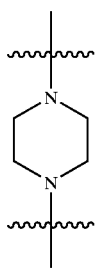

M is an alkyl group containing 1–6 carbon atoms, X is N, Y is CH, $R^1$ and $R^5$ are H and $R^2$ is Cl.

14. A pharmaceutical composition comprising as an active ingredient a compound of claim 1.

15. The pharmaceutical composition of claim 14 for use in treating inflammation, allergy, allergic rhinitis, nasal congestion, as well as allergy-induced airway responses.

16. A method of treating inflammation, allergy, nasal congestion as well as allergy-induced airway responses, said method comprising administering to a mammalian patient in need of such treatment a pharmaceutical composition which comprises therapeutically effective amounts of a compound of claim 1.

17. A method of preparing a pharmaceutical composition for treating inflammation, allergy, nasal congestion, as well as allergy-induced airway responses, said method comprising bringing into intimate contact a compound of claim 1 and a pharmaceutically acceptable carrier.

18. A compound exhibiting $H_3$ antagonist activity, or enantiomers, stereoisomers and tautomers of said compound, or pharmaceutically acceptable salts or solvates of said compound, said compound being selected from the compounds of structures listed below:

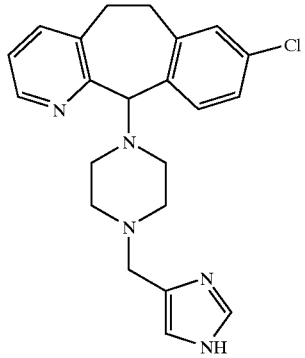

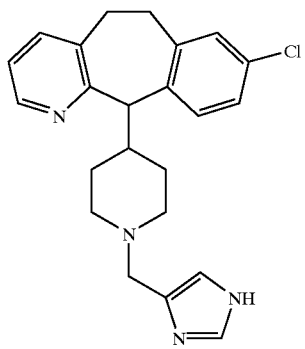

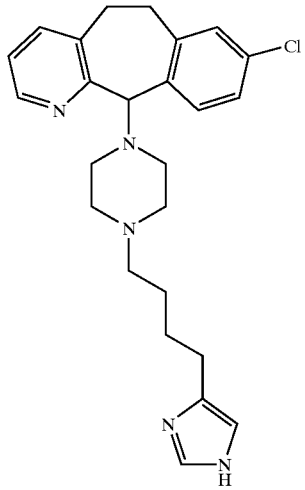

-continued
73
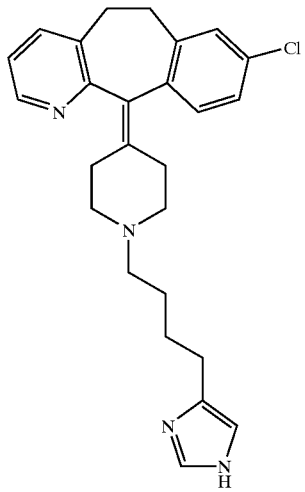
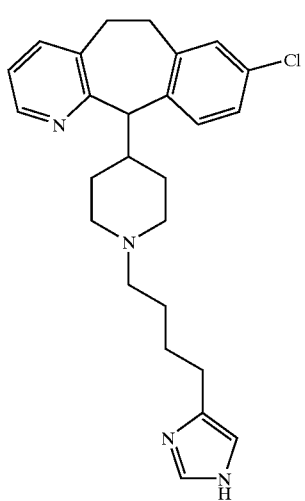
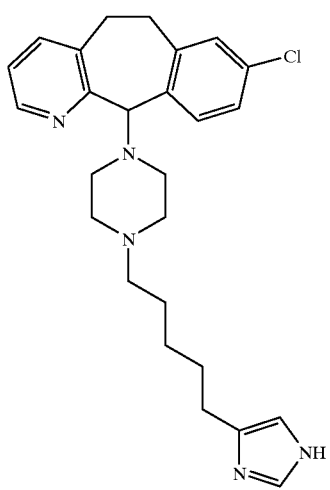
-continued
74
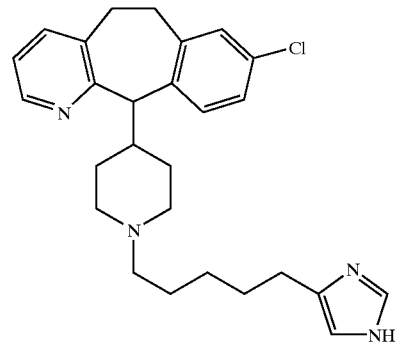
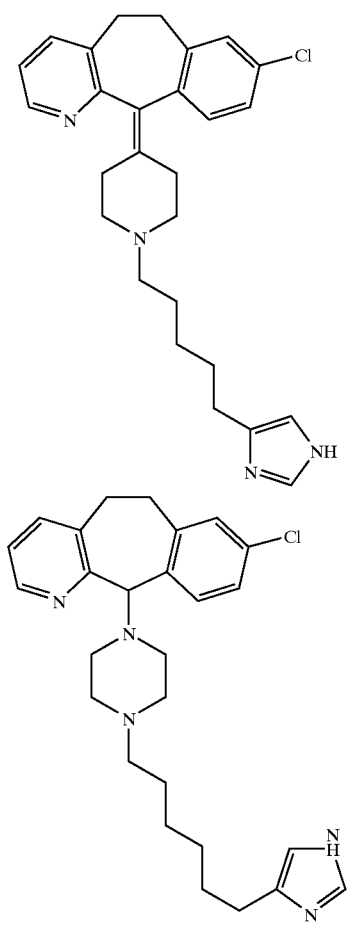
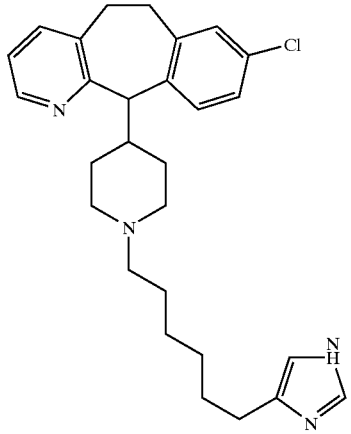

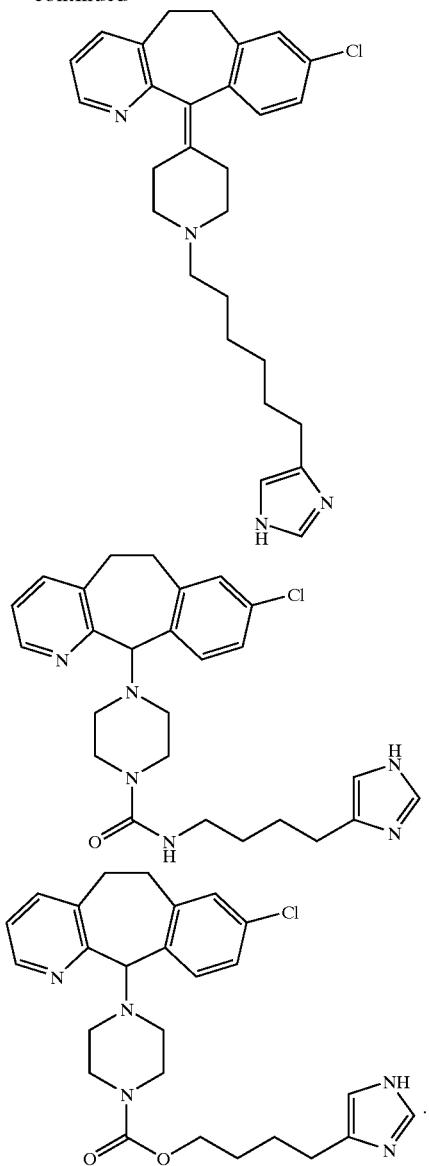
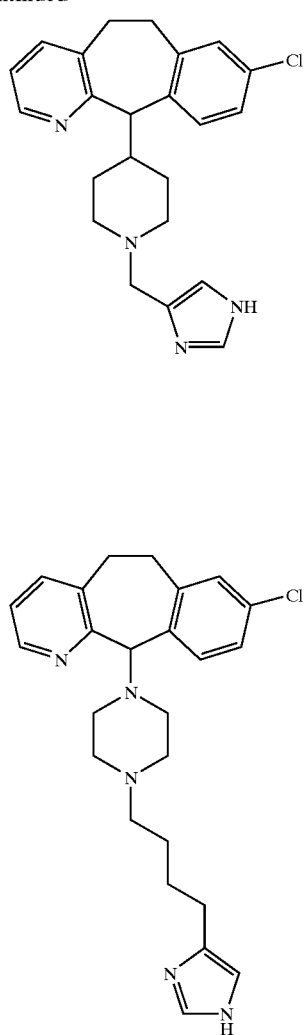
19. A compound exhibiting both $H_1$ and $H_3$ antagonist activity, or enantiomers stereoisomers and tautomers of said compound or pharmaceutically acceptable salts or solvates of said compound, said compound being selected from the compounds of structures listed below:
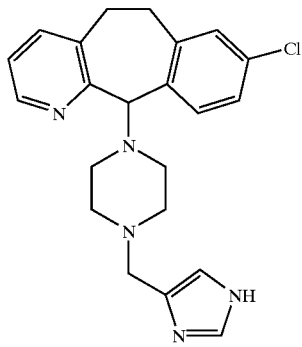
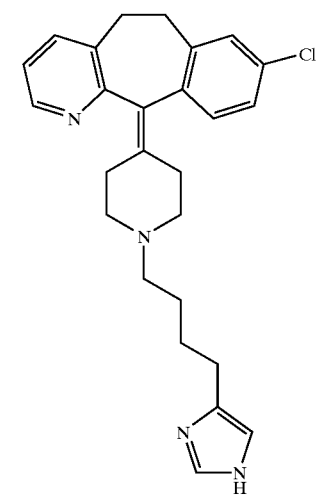

-continued
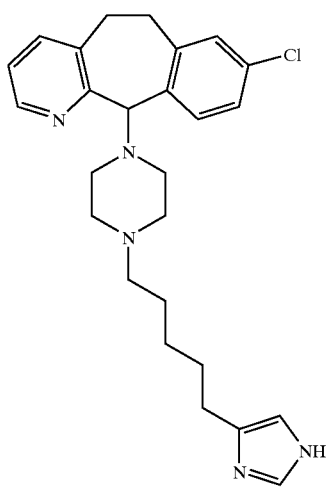
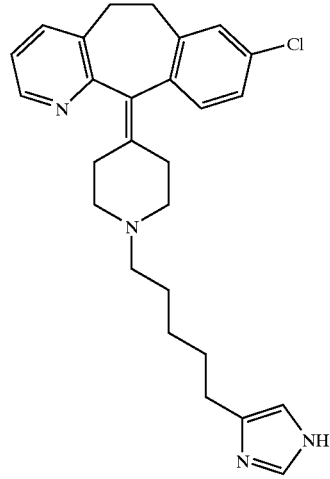
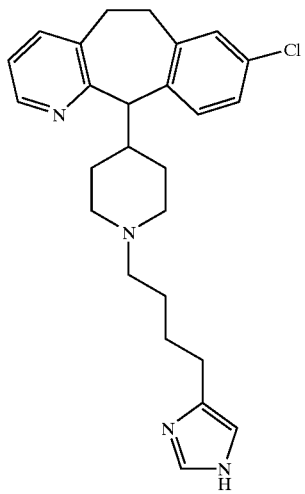
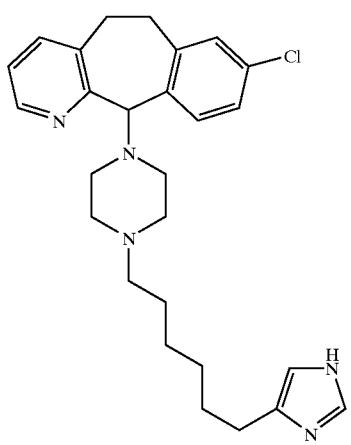
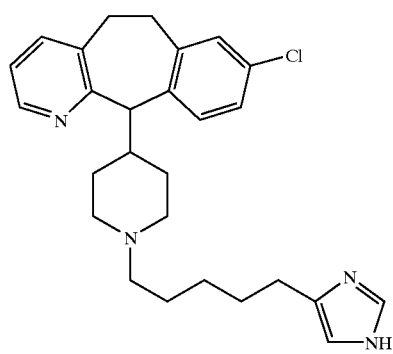
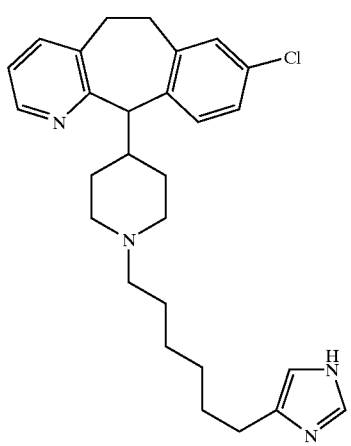

-continued

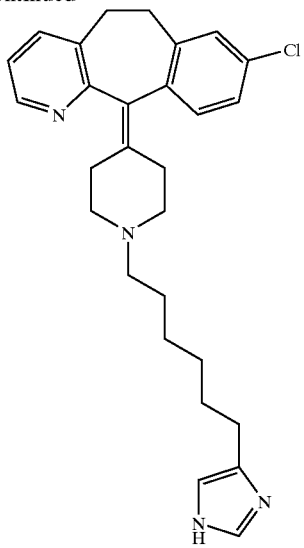

20. A compound exhibiting $H_1$ antagonist activity, or enantiomers, stereoisomers and tautomers of said compound, or pharmaceutically acceptable salts or solvates of said compound, said compound being selected from the compounds of structures listed below:

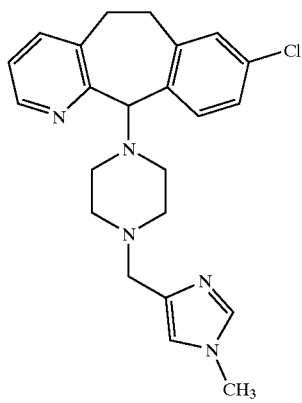

-continued

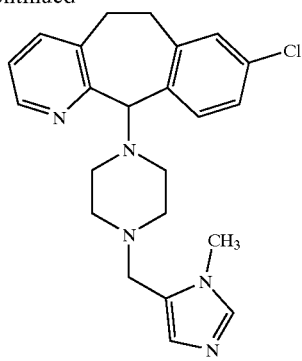

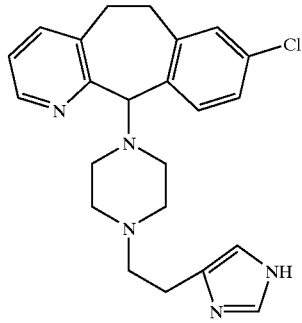

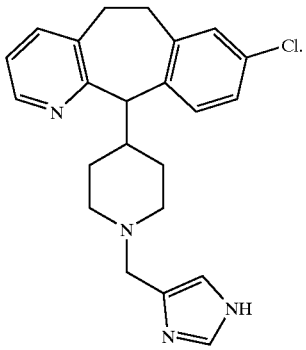

21. A pharmaceutical composition for treating inflammation, allergy, nasal congestion as well as allergy-induced airway responses, said composition comprising therapeutically effective amount of a compound of claim 18, claim 19 or claim 20 and a pharmaceutically acceptable carrier.

* * * * *